(12) United States Patent
BaMaung et al.

(10) Patent No.: US 6,323,228 B1
(45) Date of Patent: Nov. 27, 2001

(54) 3-SUBSTITUTED INDOLE ANGIOGENESIS INHIBITORS

(75) Inventors: Nwe Y. BaMaung, Niles, IL (US); Richard A. Craig, Racine, WI (US); Megumi Kawai, Libertyville; Jieyi Wang, Gurnee, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/663,005

(22) Filed: Sep. 15, 2000

(51) Int. Cl.[7] ............... A61K 31/40; C07D 209/00; C07D 209/36; C07D 417/00; A61P 43/00

(52) U.S. Cl. ............ 514/365; 548/491; 548/483; 548/484; 548/181; 548/312.1; 514/357; 514/314; 514/397; 546/278.1; 546/164

(58) Field of Search ..................... 548/491, 483, 548/484, 181, 312.1; 514/365, 314, 397, 357; 546/278.1, 164

(56) References Cited

PUBLICATIONS

Chemical Abstacts, Compound 44 and 45, 2000, Salor.*
Hiremath, et. al., 1988, Indian Journal of Chemisty Section B., 1102–1105.*
Rajshekhar, et. al., 1998, Asian Journal of Chemistry, 306–311.*
Chemical Abstacts, Compounds 2–43, 2000, Chemstar Product List.*
Chemical Abstracts, Compound 1, 2000, AsInEx Compound Collection.*
J. M. Cherrington, et al., New Paradigms for the Treatment of Cancer: The Role of Anti–Angiogenesis Agentsl,*Advances in Cancer Research*, 79:1–38 (2000).

* cited by examiner

*Primary Examiner*—Joseph K. McKane
*Assistant Examiner*—Andrea M D'Souza
(74) *Attorney, Agent, or Firm*—B. Gregory Donner; Gregory Steele

(57) ABSTRACT

3-Substituted indole carbohydrazides having the formula

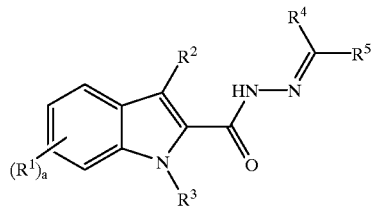

are useful for inhibiting angiogenesis. Also disclosed are angiogenesis-inhibiting compositions and methods of inhibiting angiogenesis in a mammal.

30 Claims, No Drawings

3-SUBSTITUTED INDOLE ANGIOGENESIS INHIBITORS

TECHNICAL FIELD

The instant invention relates to 3-substituted indole carbohydrazides which are useful for treating angiogenesis, methods of making the compounds, compositions containing the compounds, and methods of treatment using the compounds.

BACKGROUND OF THE INVENTION

Angiogenesis, the process by which new blood vessels are formed, is essential for normal body activities including reproduction, development, and wound repair. Although the process is not completely understood, it is believed to involve a complex interplay of molecules which regulate the growth of endothelial cells (the primary cells of capillary blood vessels). Under normal conditions, these molecules appear to maintain the microvasculature in a quiescent state (i.e., one of no capillary growth) for prolonged periods which may last for weeks or, in some cases, decades. When necessary (such as during wound repair), these same cells can undergo short bursts of growth and rapid proliferation (*J. Biol. Chem.* 1992, 267,10931–10934, and *Science* 1987, 235, 442–447.

While it is normally a regulated process, many diseases (characterized as angiogenic diseases) are driven by persistent, unregulated angiogenesis. Ocular neovascularization has been implicated as the most common cause of blindness and is responsible for approximately twenty different eye diseases. In certain existing conditions, such as arthritis, newly formed capillary blood vessels invade the joints and destroy cartilage. The growth and metastasis of solid tumors are also dependent on angiogenesis (*Cancer Res.* 1986, 46, 467–473, and *J. Natl. Cancer Inst.* 1989, 82, 4–6). It has been shown that solid tumors cannot grow beyond 1 to 2 cubic millimeters without inducing the formation of new blood vessels. Once these new blood vessels become embedded in the tumor, they provide a means for tumor cells to enter the circulation and metastasize to distant sites such as the liver, the lungs, or the bones (*N. Engl. J. Med.* 1991, 324, 1–8).

Several angiogenesis inhibitors are currently under development for use in treating angiogenic diseases, but there are disadvantages associated with these compounds. Fumagillin, a compound secreted by the fungus *Aspergillus fumigatis fresenius*, has demonstrated angioinhibitory effects, but has not been developed clinically due to the dramatic weight loss suffered by laboratory animals after prolonged exposure. TNP-470, a synthetic analog of fumagillin, also inhibits endothelial growth, but has been shown to induce asthenial and neurocortical toxicity in humans, limiting allowable dosages (*J. Clin. Oncology* 1999, 17, 2541).

As shown by these examples, there is still a need for compounds useful in treating angiogenic diseases which have improved profiles of activity. More specifically, there is a need for angiogenesis inhibitors which are safe for therapeutic use and which exhibit selective toxicity with respect to the pathological condition such as by selectively inhibiting the proliferation of endothelial cells while exhibiting no or a low degree of toxicity to normal (i.e. non-cancerous) cells. Such compounds should also be easily and cost-effectively made.

SUMMARY OF THE INVENTION

In its principle embodiment, therefore, the instant invention provides angiogenesis inhibitors of formula (I)

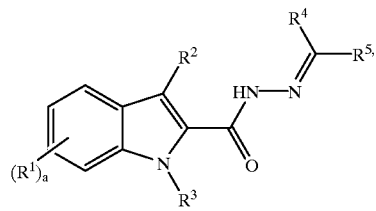

(I)

or therapeutically acceptable salts thereof, wherein a is 0, 1, 2, 3, or 4;

each $R^1$ is independently selected from the group consisting of alkoxy, amino, halo, hydroxy, and nitro;

$R^2$ is selected from the group consisting of alkenyl, alkyl, alkynyl, aryl, and heterocycle;

$R^3$ is selected from the group consisting of hydrogen, alkyl, and a nitrogen protecting group; and $R^4$ and $R^5$ are independently selected from the group consisting of hydrogen, alkyl, aryl, arylalkyl, cycloalkyl, (cycloalkyl)alkyl, heterocycle, and (heterocycle)alkyl; with the proviso that one of $R^4$ and $R^5$ is hydrogen.

In another embodiment, the instant invention provides a pharmaceutical composition comprising a compound of formula (I) or a therapeutically acceptable salt thereof, in combination with a therapeutically acceptable carrier.

In another embodiment, the instant invention provides a method of inhibiting angiogenesis in a mammal in recognized need of such treatment comprising administering to the mammal a therapeutically acceptable amount of a compound of formula (I), or a therapeutically acceptable salt thereof.

DETAILED DESCRIPTION OF THE INVENTION

Compounds of the instant invention comprise 3-substituted indole carbohydrazides which are useful for the treatment of angiogenesis-mediated diseases.

As used in the instant specification the following terms have the meanings indicated:

The term "alkanoyl," as used herein, represents an alkyl group attached to the parent molecular moiety through a carbonyl group.

The term "alkenyl," as used herein, represents a monovalent straight or branched chain group of two to six carbon atoms containing at least one carbon-carbon double bond.

The term "alkoxy," as used herein, represents an alkyl group attached to the parent molecular moiety through an oxygen atom.

The term "alkoxyalkyl," as used herein, represents an alkoxy group attached to the parent molecular moiety through an alkyl group.

The term "alkoxycarbonyl," as used herein, represents an alkoxy group attached to the parent molecular moiety through a carbonyl group.

The term "alkyl," as used herein, represents a monovalent group of one to six carbon atoms derived from a straight or branched chain saturated hydrocarbon by the removal of a single hydrogen atom.

The term "alkylsulfonyl," as used herein, represents an alkyl group attached to the parent molecular moiety through a sulfonyl group.

The term "alkynyl," as used herein, represents a monovalent straight or branched chain group of two to six carbon atoms containing at least one carbon-carbon triple bond.

The term "amido," as used herein, represents an amino group attached to the parent molecular moiety through a carbonyl group.

The term "amino," as used herein, represents —NR$^6$R$^7$, wherein R$^6$ and R$^7$ are independently selected from the group consisting of hydrogen, alkanoyl, alkenyl, alkyl, cycloalkyl, (cycloalkyl)alkyl, a nitrogen protecting group, and phenyl; or R$^6$ and R$^7$, together with the nitrogen atom to which they are attached, form a ring selected from the group consisting of morpholinyl, piperazinyl, piperidinyl, pyrrolidinyl, thiomorpholinyl, and thiomorpholinyl dioxide.

The term "aminosulfonyl," as used herein, represents an amino group attached to the parent molecular moiety through a sulfonyl group.

The term "aminosulfonyloxy," as used herein, represents an aminosulfonyl group attached to the parent molecular moiety through an oxygen atom.

The term "aryl," as used herein, represents dihydronaphthyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of this invention can be optionally substituted with one, two, three, four, or five substituents independently selected from the group consisting of alkanoyl, alkenyl, alkoxy, alkoxyalkyl, alkoxycarbonyl, alkyl, alkylsulfonyl, amido, amino, aminosulfonyl, aminosulfonyloxy, carbonyloxy, cyano, cycloalkyl, (cycloalkyl)alkyl, formyl, halo, haloalkoxy, haloalkyl, hydroxy, hydroxyalkyl, nitro, perfluoroalkoxy, perfluoroalkyl, and thioalkoxy.

The term "arylalkyl," as used herein, represents an aryl group attached to the parent molecular moiety through an alkyl group.

The term "carbonyl," as used herein, represents —C(O)—.

The term "carbonyloxy," as used herein, represents an alkanoyl group attached to the parent molecular moiety through an oxygen atom.

The term "carbonyloxyalkyl," as used herein, represents a carbonyloxy group attached to the parent molecular moiety through an alkyl group.

The term "cyano," as used herein, represents —CN.

The term "cycloalkyl," as used herein, represents a saturated cyclic, bicyclic, or tricyclic hydrocarbon ring system having three to twelve carbon atoms. Examples of cycloalkyl groups include cyclopropyl, cyclopentyl, bicyclo[3.1.1]heptyl, adamantyl, and the like.

The term "(cycloalkyl)alkyl," as used herein, represents a cycloalkyl group attached to the parent molecular moiety through an alkyl group.

The term "formyl," as used herein, represents —CHO.

The term "halo," as used herein, represents F, Cl, Br, or I.

The term "haloalkoxy," as used herein, represents a haloalkyl group attached to the parent molecular moiety through an oxygen atom.

The term "haloalkyl," as used herein, represents an alkyl group substituted by one, two, three, or four halogen atoms.

The term "heterocycle," as used herein, represents a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group. The heterocycle groups of this invention can be attached through a carbon atom or a nitrogen atom in the ring. The heterocycle groups of this invention can also be optionally substituted with one, two, three, or four substituents independently selected from the group consisting of alkanoyl, alkenyl, alkoxy, alkoxyalkyl, alkoxycarbonyl, alkyl, alkylsulfonyl, amido, amino, aminosulfonyl, aryl, carbonyloxy, carbonyloxyalkyl, cyano, cycloalkyl, (cycloalkyl)alkyl, formyl, halo, haloalkoxy, haloalkyl, hydroxy, hydroxyalkyl, nitro, perfluoroalkoxy, perfluoroalkyl, and thioalkoxy.

The term "(heterocycle)alkyl," as used herein, represents a heterocycle group attached to the parent molecular moiety through an alkyl group.

The term "hydroxy," as used herein, represents —OH.

The term "hydroxyalkyl," as used herein, represents a hydroxy group attached to the parent molecular moiety through an alkyl group.

The term "nitro," as used herein, represents —NO$_2$.

The term "nitrogen protecting group," as used herein, represents groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, α-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, and the like.

The term "perfluoralkoxy," as used herein, represents a perfluoroalkyl group attached to the parent molecular moiety through an oxygen atom.

The term "perfluoroalkyl," as used herein, represents an alkyl group wherein each hydrogen radical bound to the alkyl group has been replaced by a fluoride radical.

The term "prodrug," refers to compounds which are rapidly transformed in vivo to parent compounds of formula (I) for example, by hydrolysis in blood.

The term "sulfonyl," as used herein, represents —SO$_2$—.

The term "thioalkoxy," as used herein, represents an alkyl group attached to the parent molecular moiety through a sulfur atom.

The instant compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The term "therapeutically acceptable salt," as use herein, represents those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the instant invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2 hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include calcium, lithium, magnesium, potassium, sodium, and the like, as well as non-toxic ammonium, quaternary ammonium, and amine cations, including, but not limited to, ammonium, dimethylamine, ethylamine, methylamine, tetraethylammonium, tetramethylammonium, triethylamine, trimethylamine, and the like.

In accordance with methods of treatment and pharmaceutical compositions of the invention, the compounds can be administered alone or in combination with other angiogenesis-inhibiting agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The inhibitory effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefor.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred embodiments of the instant invention include, but are not limited to: compounds of formula (I), wherein $R^2$ is alkenyl, alkyl, or aryl; and compounds of formula (I), wherein one of $R^4$ and $R^5$ is alkyl, aryl, or heterocycle.

Determination of Biological Activity

Human neonatal dermal microvascular endothelial cells (HMVEC) and their recommended culture media (EGM2) were purchased from Clonetics (San Diego, Calif.). Cells were grown in EGM2 with 5% FBS according to instructions provided by Clonetics. Cell proliferation assays were performed in 96-well plates using cells between passages 6 and 12. Cells were seeded at 3000–5000 cells/well in 180 μL/well EGM2 with 5% FBS and were allowed to attach for 4 hours at 5% $CO_2$ in a 37° C. incubator. All compounds were dissolved in DMSO at 10 mM and were diluted with 50 mM Hepes buffer (pH 7.4) in 100 mM NaCl to final concentrations of 0.01 μM, 0.1 μM, 1 μM, 10 μM, 100 μM, and 1000 μM. Each well of the culture plate was treated with 20 μL of the diluents resulting in final concentrations of 0.001 μM, 0.01 μM, 0.1 μM, 1 μM, 10 μM, and 100 μM. The cells were returned to 5% $CO_2$ in a 37° C. incubator for 3 days. Live cells were quantitated with MTS reagents (Promega, Madison Wis.). $IC_{50}$ values were calculated from dose response curves. All compounds had $IC_{50}$ values <30 μM with a preferred range of 0.1 μM–0.5 μM and a most preferred range of 9 nM–50 nM. As it has been shown that SU5416, a small molecule which inhibits endothelial cell proliferation, has good in vivo activity against certain tumor models, it can therefore be extrapolated that the compounds of the invention, including but not limited to those specified in the examples, are useful for the treatment of diseases caused or exascerbated by angiogenesis (*Adv. Cancer Res.* 2000, 79, 1–38).

As angiogenesis inhibitors, these compounds are useful in the treatment of both primary and metastatic solid tumors and carcinomas of, for example, the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, solid tumors arising from hematopoietic malignancies including leukemias and chloromas, plasmacytomas, plaques, tumors of mycosis fungoides, cutaneous T-cell lymphoma/leukemia, lymphomas including Hodgkin's and non-Hodgkin's lymphomas, prophylaxis of autoimmune diseases including rheumatoid, immune and degenerative arthritis, ocular diseases including diabetic retinopathy, retinopathy of prematurity, corneal graft rejection, retrolental fibroplasia, neovascular glaucoma, rubeosis, retinal neovascularization due to macular degeneration, hypoxia, abnormal neovascularization conditions of the eye, skin diseases including psoriasis, blood vessel diseases including hemagiomas and capillary proliferation within atherosclerotic plaques, Osler-Webber Syndrome, myocardial angiogenesis, plaque neovascularization, telangiectasia, hemophiliac joints, angiofibroma, and wound granulation.

Synthetic Methods

Abbreviations which have been used in the descriptions of the scheme and the examples that follow are: THF for tetrahydrofuran, and DMSO for dimethylsulfoxide.

The compounds and processes of the instant invention will be better understood in connection with the following synthetic schemes which illustrate methods by which the compounds of the invention can be prepared. The compounds defined above can be prepared by a variety of synthetic routes. Representative procedures are shown in Scheme 1. The groups $R^1$, $R^2$, $R^3$, $R^4$, and $R^5$ are defined above. It will be readily apparent to one of ordinary skill in the art that the compounds defined above can be synthesized by substitution of the appropriate reactants and agents in the syntheses shown below.

Scheme 1

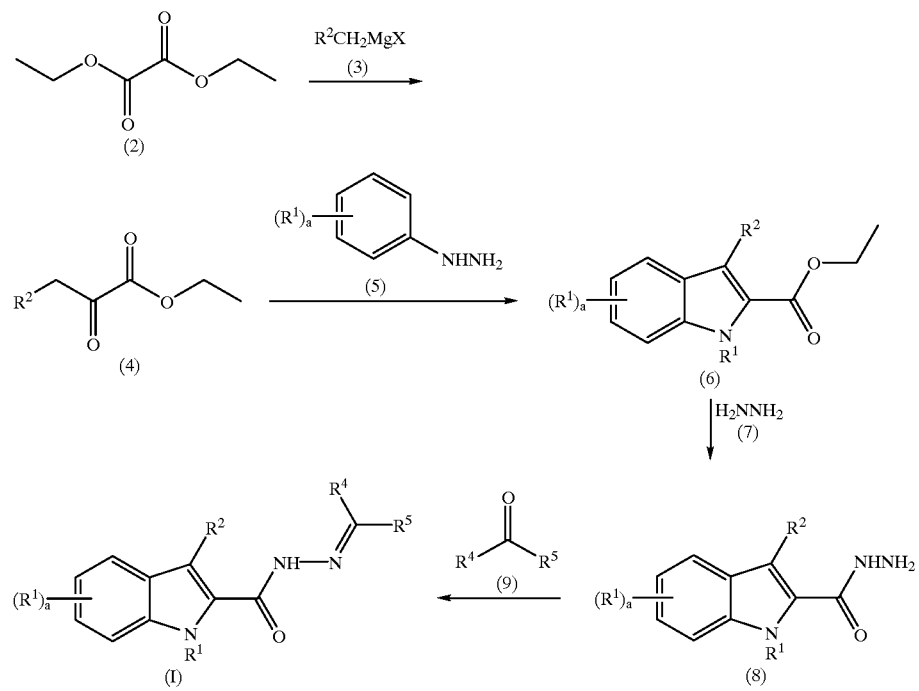

As shown in Scheme 1, compounds of formula (2) can be reacted with compounds of formula (3) (X is Cl, Br, or I) to provide compounds of formula (4).

Examples of solvents used in these reactions include diethyl ether, THF, and methyl tert-butyl ether. The reaction is conducted at about −100° C. to 0° C. and depends on the solvent chosen. Reaction times are typically about 20 to about 60 minutes.

Compounds of formula (4) can be reacted with compounds of formula (5) in the presence of acid to provide compounds of formula (6) ($R^1$ is H). Representative acids include sulfuric acid, hydrochloric acid, and acetic acid. Examples of solvents used in these reactions include ethanol, isopropanol, and methanol. The reaction is conducted at about 60° C. to about 130° C. Reaction times are typically about 30 minutes to about 2 hours.

Conversion of compound of formula (6) ($R^1$ is H) to compounds of formula (8) ($R^1$ is H) can be accomplished by treatment with hydrazine (7) or hydrazine hydrate. Examples of solvents used in these reactions include ethanol, isopropanol, and methanol. The reaction is conducted at about 60° C. to about 95° C. and depends on the solvent chosen. Reaction times are typically about 12 to about 24 hours.

Compounds of formula (8) ($R^1$ is H) can be condensed with compounds of formula (9) to provide compounds of formula (I) ($R^1$ is H). Examples of solvents used in these reactions include ethanol, methanol, and isopropanol. The reaction is conducted at about 60° C. to about 95° C. and depends on the solvent chosen. Reaction times are typically about 12 to about 24 hours.

Compounds of formula (I) ($R^1$ is H) can be intraconverted to compounds of formula (I) ($R^1$ is alkyl or a nitrogen protecting group) by methods known to those of ordinary skill in the art.

The instant invention will now be described in connection with certain preferred embodiments which are not intended to limit its scope. On the contrary, the instant invention covers all alternatives, modifications, and equivalents as can be included within the scope of the claims. Thus, the following examples, which include preferred embodiments, will illustrate the preferred practice of the instant invention, it being understood that the examples are for the purposes of illustration of certain preferred embodiments and are presented to provide what is believed to be the most useful and readily understood description of its procedures and conceptual aspects.

EXAMPLE 1

N'-((4-methoxyphenyl)methylidene)-3-phenyl-1H-indole-2-carbohydrazide

EXAMPLE 1A ethyl 2-oxo-3-phenylpropanoate

A solution of diethyl oxalate (11.15 mL, 82.1 mmol) in diethyl ether (50 mL) at −78° C. was treated dropwise with 1 M benzylmagnesium chloride in diethyl ether (82 mL, 82 mmol) while maintaining an internal temperature of −60° C. The mixture was stirred for 30 minutes and poured into a mixture of concentrated HCl (8 mL), ice (40 mL), and diethyl ether (50 mL). The organic phase was washed with water and brine, dried ($MgSO_4$), filtered, and concentrated to provide 15.5 g (98%) of the desired product of sufficient purity for subsequent use.

EXAMPLE 1B ethyl 3-phenyl-1H-indole-2-carboxylate

A mixture of Example 1A (7.81 g, 40.7 mmol) and phenylhydrazine (4.00 mL, 40.7 mmol) was treated with concentrated sulfuric acid (4 drops), heated to 120° C. for 15 minutes, cooled to room temperature, treated with ethanol (50 mL), treated with bubbling HCl gas for 2 minutes, and heated to reflux for 1 hour. The mixture was poured into water (100 mL) and extracted with diethyl ether. The combined extracts were washed with water and brine, dried ($Na_2SO_4$), filtered, and concentrated. The concentrate was recrystallized from ethanol to provide 3.43 g (32%) of the desired product.

EXAMPLE 1C 3-phenyl-1H-indole-2-carbohydrazide

A solution of Example 1B (2.65 g, 10 mmol) in ethanol (20 mL) was treated with hydrazine hydrate (3.12 mL, 100 mmol), heated to reflux for 18 hours, cooled to room temperature, and filtered. The resulting solid was washed with ethanol and dried under vacuum to provide 1.86 g (74%) of the desired product of sufficient purity for subsequent use.

EXAMPLE 1D

N'-((4-methoxyphenyl)methylidene)-3-phenyl-1H-indole-2-carbohydrazide

A solution of Example 1C (1.76 g, 7.0 mmol) and p-anisaldehyde (894 mL, 7.35 mmol) in ethanol (120 mL) was refluxed for 18 hours, cooled to room temperature, and filtered. The resulting solid was washed with ethanol and dried under vacuum to provide 2.08 g (80%) of the desired product. MS (ESI(+)) m/e 370 $(M+H)^+$.

EXAMPLE 2

N'((4-bromophenyl)methylidene)-3-phenyl-1H-indole-2-carbohydrazide

A solution of Example 1C (1.76 g, 7.0 mmol) and 4-bromobenzaldehyde (1.36 g, 7.35 mmol) in ethanol (120 mL) was refluxed for 18 hours, cooled to room temperature, and filtered. The resulting solid was washed with ethanol and dried under vacuum to provide 2.38 g (81%) of the desired product. MS (ESI(+)) m/e 420 $(M+H)^+$; $^1$H NMR (300 MHz, DMSO-$d_6$) δ 7.09–7.16 (m, 1H), 7.26–7.57 (m, 9H), 7.58–7.72 (m, 3H), 8.05 (s, 1H).

EXAMPLE 3

3-phenyl-N'-((4-(trifluoromethoxy)phenyl)methylidene)-1H-indole-2-carbohydrazide The desired product was prepared by substituting 4-(trifluoromethoxy)benzaldehyde for 4-bromobenzaldehyde in Example 2, then purifying the resulting product by flash column chromatography on silica gel with 15% acetone/hexanes.

MS (ESI(+)) m/e 424 $(M+H)^+$; $^1$H NMR (300 MHz, DMSO-$d_6$) δ 7.10–7.16 (m, 1H), 7.25–7.58 (m, 9H), 7.65 (d, 1H), 7.73–7.92 (br s, 2H), 8.12 (s, 1H).

EXAMPLE 4

N'-((4-(difluoromethoxy)phenyl)methylidene)-3-phenyl-1H-indole-2-carbohydrazide

The desired product was prepared by substituting 4-(difluoromethoxy)benzaldehyde for 4-bromobenzaldehye in Example 2, then purifying the resulting product by flash column chromatography on silica gel with 15% acetone/hexanes.

MS (ESI(+)) m/e 406 (M+H)+; 1H NMR (300 MHz, DMSO-d6) δ 7.06–7.16 (m, 2H), 7.20–7.60 (m, 9H), 7.65 (d, 1H), 7.72–7.81 (br m, 1H), 8.07 (s, 1H).

EXAMPLE 5

N'-((3-bromophenyl)methylidene)-3-phenyl-1H-indole-2-carbohydrazide

The desired product was prepared by substituting 3-bromobenzaldehyde for 4-bromobenzaldehyde in Example 2, then purifying the resulting product by flash column chromatography on silica gel with 15% acetone/hexanes.

MS (ESI(−)) m/e 418 (M−H)−; 1H NMR (300 MHz, DMSO-d6) δ 7.11–7.17 (m, 1H), 7.25–8.86 (m, 13H).

EXAMPLE 6

N'-((4-(dihydroxyamino)phenyl)methylidene)-3-phenyl-1H-indole-2-carbohydrazide

The desired product was prepared by substituting 4-nitrobenzaldehyde for 4-bromobenzaldehyde in Example 2.

MS (ESI(+)) m/e 385 (M+H)+; 1H NMR (300 MHz, DMSO-d6) δ 7.11–7.16 (m, 1H), 7.26–7.34 (m, 1H), 7.36–7.57 (m, 6H), 7.66 (d, 1H), 7.81–8.33 (m, 5H).

EXAMPLE 7

3-phenyl-N'-(phenylmethylidene)-1H-indole-2-carbohydrazide

The desired product was prepared by substituting benzaldehyde for 4-bromobenzaldehyde in Example 2.

MS (ESI(+)) m/e 340 (M+H)+; 1H NMR (300 MHz, DMSO-d6) δ 7.09–7.15 (m, 1H), 7.26–7.58 (m, 10H), 7.62–7.75 (m, 3H), 8.07 (s, 1H).

EXAMPLE 8

N'-((3-cyanophenyl)methylidene)-3-phenyl-1H-indole-2-carbohydrazide

The desired product was prepared by substituting 3-cyanobenzaldehyde for 4-bromobenzaldehyde in Example 2.

MS (ESI(+)) m/e 365 (M+H)+; 1H NMR (300 MHz, DMSO-d6) δ 7.11–7.16 (m, 1H), 7.26–7.33 (m, 1H), 7.37–8.21 (m, 11H).

EXAMPLE 9

N'-((4-methoxyphenyl)methylidene)-3-methyl-1H-indole-2-carbohydrazide

The desired product was prepared by substituting p-anisaldehyde and Example 61C for 4-bromobenzaldehyde and Example 1C, respectively, in Example 2.

MS (ESI(+)) m/e 308 (M+H)+.

EXAMPLE 10

N'-((4-cyanophenyl)methylidene)-3-phenyl-1H-indole-2-carbohydrazide

The desired product was prepared by substituting 4-cyanobenzaldehyde for 4-bromobenzaldehyde in Example 2.

MS (ESI(+)) m/e 365 (M+H)+, 1H NMR (300 MHz, DMSO-d6) δ 7.10–7.16 (m, 1H), 7.26–7.32 (m, 1H), 7.36–7.48 (br s, 2H), 7.48–7.56 (m, 2H), 7.96 (br s, 3H), 8.11 (br s, 1H).

EXAMPLE 11

N-(4-((2-((3-phenyl-1H-indol-2-yl)carbonyl)hydrazono)methyl)phenyl)acetamide

The desired product was prepared by substituting 4-acetamidobenzaldehyde for 4-bromobenzaldehyde in Example 2.

MS (ESI(+)) m/e 397 (M+H)+; 1H NMR (300 MHz, DMSO-d6) δ 2.06 (s, 3H), 7.09–7.15 (m, 1H), 7.25–7.31 (m, 1H), 7.32–7.38 (br s, 1H), 7.40–7.70 (m, 9H), 8.00 (s, 1H).

EXAMPLE 12

N'-((4-(diethylamino)phenyl)methylidene)-3-phenyl-1H-indole-2-carbohydrazide

The desired product was prepared by substituting 4-diethylaminobenzaldehyde for 4-bromobenzaldehyde in Example 2.

MS (ESI(+)) m/e 411 (M+H)+; 1H NMR (300 MHz, DMSO-d6) δ 1.10 (br t, 6H), 3.34–3.41 (br m, 4 H), 6.52–6.73 (m, 2H), 7.08–7.15 (m, 1H), 7.25–7.29 (m, 1H), 7.30–7.38 (m, 1H), 7.40–7.57 (m, 6H), 7.62 (d, 1H), 7.87 (s, 1H).

EXAMPLE 13

N'-((4-isopropylphenyl)methylidene)-3-phenyl-1H-indole-2-carbohydrazide

The desired product was prepared by substituting 4-isopropylbenzaldehyde for 4-bromobenzaldehyde in Example 2.

MS (ESI(+)) m/e 382 (M+H)+; 1H NMR (300 MHz, DMSO-d6) δ 1.20 (d, 6H), 2.92 (br m, 1H), 7.10–7.15 (m, 1H), 7.25–7.67 (m, 12H), 8.03 (s, 1H).

EXAMPLE 14

N'-((3-nitrophenyl)methylidene)-3-phenyl-1H-indole-2-carbohydrazide

The desired product was prepared by substituting 3-nitrobenzaldehyde for 4-bromobenzaldehyde in Example 2.

MS (ESI(−)) m/e 383 (M−H)−; 1H NMR (300 MHz, DMSO-d6) δ 7.11–7.16 (m, 1H), 7.26–7.33 (t, 1H), 7.35–7.60 (m, 5H), 7.63–7.77 (m, 2H), 7.96–8.60 (br m, 3H).

EXAMPLE 15

3-phenyl-N'-((4-(1-pyrrolidinyl)phenyl)methylidene)-1H-indole-2-carbohydrazide

The desired product was prepared by substituting 4-pyrrolidinobenzaldehyde for 4-bromobenzaldehyde in Example 2.

MS (ESI(+)) m/e 409 (M+H)+; 1H NMR (300 MHz, DMSO-d6) δ 1.95 (br s, 4H), 6.53–6.63 (br m, 2H), 7.09–7.14 (m, 1H), 7.24–7.30 (m, 1H), 7.32–7.37 (br m, 1H), 7.40–7.58 (m, 7H), 7.63 (br d, 1H), 7.88 (s, 1H).

EXAMPLE 16

N'-((4-(methylsulfonyl)phenyl)methylidene)-3-phenyl-1H-indole-2-carbohydrazide

The desired product was prepared by substituting 4-methylsulfonylbenzaldehyde for 4-bromobenzaldehyde in Example 2.

MS (ESI(−)) m/e 416 (M−H)⁻; $^1$H NMR (300 MHz, DMSO-$d_6$) δ 3.23 (s, 3H), 7.11–7.16 (m, 1H), 7.26–7.33 (t, 1H), 7.37–7.60 (m, 5H), 7.65 (d, 1H), 7.84–8.05 (br m, 3H), 8.14 (br s, 1H).

EXAMPLE 17

N'-(butylidene)-3-phenyl-1H-indole-2-carbohydrazide

The desired product was prepared by substituting butyraldehyde for 4-bromobenzaldehyde in Example 2.

MS (ESI(+)) m/e 306 (M+H)⁺; $^1$H NMR (300 MHz, DMSO-$d_6$) δ 0.85–0.95 (br m, 3H), 1.41–1.55 (br m, 2H), 2.14–2.25 (br m, 2H), 7.07–7.15 (m, 1H), 7.23–7.53 (m, 8H), 7.60 (d, 1H).

EXAMPLE 18

N'-(pentylidene)-3-phenyl-1H-indole-2-carbohydrazide

The desired product was prepared by substituting pentanal for 4-bromobenzaldehyde in Example 2.

MS (ESI(+)) m/e 320 (M+H)⁺; $^1$H NMR (300 MHz, DMSO-$d_6$) δ 0.80–0.93 (br m, 3H), 1.21–1.48 (m, 4H), 2.15–2.27 (br m, 2H), 7.06–7.14 (m, 1H), 7.20–7.53 (m, 7H), 7.60 (d, 1H).

EXAMPLE 19

N'-((4-chlorophenyl)methylidene)-3-phenyl-1H-indole-2-carbohydrazide

The desired product was prepared by substituting 4-chlorobenzaldehyde for 4-bromobenzaldehyde in Example 2.

MS (ESI(+)) m/e 374 (M+H)⁺; $^1$H NMR (300 MHz, DMSO-$d_6$) δ 7.10–7.16 (m, 1H), 7.26–7.33 (t, 1H), 7.37–7.77 (m, 11H), 8.06 (br s, 1H).

EXAMPLE 20

N'-((4-bromophenyl)methylidene)-3-isopropyl-1H-indole-2-carbohydrazide

EXAMPLE 20A ethyl 4-methyl-2-oxopentanoate

The desired product was prepared by substituting isobutylmagnesium bromide for benzylmagnesium chloride in Example 1A.

EXAMPLE 20B ethyl 3-isopropyl-1H-indole-2-carboxylate

The desired product was prepared by substituting Example 20A for Example 1A in Example 1B, then purifying the resulting product by flash column chromatography on silica gel with 0–10% ethyl acetate/n-hexane.

EXAMPLE 20C 3-isopropyl-1H-indole-2-carbohydrazide

The desired product was prepared by substituting Example 20B for Example 1B in Example 1C, then purifying the resulting product by flash column chromatography on silica gel with 0–20% acetone/n-hexane.

EXAMPLE 20D

N'-((4-bromophenyl)methylidene)-3-isopropyl-1H-indole-2-carbohydrazide

The desired product was prepared by substituting Example 20C for Example 1C in Example 2.

MS (ESI(−)) m/e 384 (M−H)⁻; $^1$H NMR (300 MHz, DMSO-$d_6$) δ 1.40 (d, 6H), 3.82 (br m, 1H), 7.00–7.06 (m, 1H), 7.17–7.25 (m, 1H), 7.40–7.45 (m, 1H), 7.67 (s, 4H), 7.78–7.83 (m, 3H), 8.32 (br s, 1H).

EXAMPLE 21

N'-((4-chlorophenyl)methylidene)-3-isopropyl-1H-indole-2-carbohydrazide

The desired product was prepared by substituting Example 20C and 4-chlorobenzaldehyde for Example 1C and 4-bromobenzaldehyde, respectively, in Example 2.

MS (ESI(+)) m/e 340 (M+H)⁺; $^1$H NMR (300 MHz, DMSO-$d_6$) δ 1.40 (d, 6H), 3.82 (br m, 1H), 6.99–7.06 (m, 1H), 7.17–7.24 (m, 1H), 7.40–7.45 (m, 1H), 7.49–7.55 (m, 2H), 7.70–7.83 (m, 3H), 8.32 (br s, 1H).

EXAMPLE 22

N'-((4-fluorophenyl)methylidene)-3-isopropyl-1H-indole-2-carbohydrazide

The desired product was prepared by substituting Example 20C and 4-fluorobenzaldehyde for Example 1C and 4-bromobenzaldehyde, respectively, in Example 2.

MS (ESI(+)) m/e 324 (M+H)⁺; $^1$H NMR (300 MHz, DMSO-$d_6$) δ 1.39 (dd, 6H), 3.79 (br m, 1H), 6.96–7.06 (m, 1H), 7.14–7.25 (m, 1H), 7.25–7.35 (m, 2H), 7.38–7.46 (m, 1H), 7.74–7.83 (m, 3H), 8.33 (br s, 1H).

EXAMPLE 23

N'-((4-bromophenyl)methylidene)-5-fluoro-3-phenyl-1H-indole-2-carbohydrazide

EXAMPLE 23A ethyl 5-fluoro-3-phenyl-1H-indole-2-carboxylate

The desired product was prepared by substituting 4-fluorophenylhydrazine for phenylhydrazine in Example 1B.

EXAMPLE 23B 5-fluoro-3-phenyl-1H-indole-2-carbohydrazide

The desired product was prepared by substituting Example 23A for Example 1B in Example 1C.

EXAMPLE 23C

N'-((4-bromophenyl)methylidene)-5-fluoro-3-phenyl-1H-indole-2-carbohydrazide

The desired product was prepared by substituting Example 23B for Example 1C in Example 2.

MS (ESI(+)) m/e 437 (M+H)⁺; $^1$H NMR (300 MHz, DMSO-$d_6$) δ 7.11–7.19 (m, 2H), 7.30–7.36 (m, 1H), 7.42–7.56 (m, 6H), 7.59–7.70 (br s, 2H), 7.72–7.86 (m, 2H), 8.07 (br s, 1H).

EXAMPLE 24

N'-((4-chlorophenyl)methylidene)-5-fluoro-3-phenyl-1H-indole-2-carbohydrazide

The desired product was prepared by substituting Example 23B and 4-chlorobenzaldehyde for Example 1C and 4-bromobenzaldehyde, respectively, in Example 2.

MS (ESI(+)) m/e 392 (M+H)$^+$; $^1$H NMR (300 MHz, DMSO-d$_6$) δ 7.11–7.20 (m, 2H), 7.29–7.56 (m, 8H), 7.65–7.77 (br m, 2H), 8.08 (br s, 1H).

EXAMPLE 25

5-fluoro-N'-((4-fluorophenyl)methylidene)-3-phenyl-1H-indole-2-carbohydrazide

The desired product was prepared by substituting Example 23B and 4-fluorobenzaldehyde for Example 1C and 4-bromobenzaldehyde, respectively, in Example 2.

MS (ESI(+)) m/e 376 (M+H)$^+$; $^1$H NMR (300 MHz, DMSO-d$_6$) δ 7.11–7.20 (m, 2H), 7.22–7.56 (m, 8H), 7.71–7.83 (br m, 2H), 8.08 (br s, 1H).

EXAMPLE 26

N'-((4-bromophenyl)methylidene)-5-methoxy-3-phenyl-1H-indole-2-carbohydrazide

EXAMPLE 26A ethyl 5-methoxy-3-phenyl-1H-indole-2-carboxylate

The desired product was prepared by substituting 4-methoxyphenylhydrazine for phenylhydrazine in Example 1B, collecting the resulting precipitate by filtration, and purifying the resulting product by recrystallization from ethanol.

EXAMPLE 26B 5-methoxy-3-phenyl-1H-indole-2-carbohydrazide

The desired product was prepared by substituting Example 26A for Example 1B in Example 1C.

EXAMPLE 26C

N'-((4-bromophenyl)methylidene)-5-methoxy-3-phenyl-1H-indole-2-carbohydrazide

The desired product was prepared by substituting Example 26B for Example 1C in Example 2.

MS (ESI(+)) m/e 450 (M+H)$^+$; $^1$H NMR (300 MHz, DMSO-d$_6$) δ 3.75 (s, 3H), 6.95 (dd, 1H), 7.26–7.70 (m, 11H), 8.03 (br s, 1H).

EXAMPLE 27

N'-((4-chlorophenyl)methylidene)-5-methoxy-3-phenyl-1H-indole-2-carbohydrazide

The desired product was prepared by substituting Example 26B and 4-chlorobenzaldehyde for Example 1C and 4-bromobenzaldehyde, respectively, in Example 2.

MS (ESI(+)) m/e 404 (M+H)$^+$; $^1$H NMR (300 MHz, DMSO-d$_6$) δ 3.75 (s, 3H), 6.94 (dd, 1H), 7.03 (br m, 1H), 7.26–7.56 (m, 9H), 7.78 (br m, 1H), 8.05 (br s, 1H).

EXAMPLE 28

N'-((4-fluorophenyl)methylidene)-5-methoxy-3-phenyl-1H-indole-2-carbohydrazide

The desired product was prepared by substituting Example 26B and 4-fluorobenzaldehyde for Example 1C and 4-bromobenzaldehyde, respectively, in Example 2.

MS (ESI(+)) m/e 388 (M+H)$^+$; $^1$H NMR (300 MHz, DMSO-d$_6$) δ 3.75 (s, 3H), 6.86–7.07 (m, 2H), 7.22–7.56 (m, 9H), 7.73 (br m, 1H), 8.05 (br s, 1H).

EXAMPLE 29

5-bromo-N'-((4-bromophenyl)methylidene)-3-phenyl-1H-indole-2-carbohydrazide

EXAMPLE 29A ethyl 5-bromo-3-phenyl-1H-indole-2-carboxylate

The desired product was prepared by substituting 4-bromophenylhydrazine hydrochloride for phenylhydrazine in Example 1B, collecting the resulting precipitate by filtration, washing the solid with ethanol, and drying under vacuum.

EXAMPLE 29B 5-bromo-3-phenyl-1H-indole-2-carbohydrazide

The desired product was prepared by substituting Example 29A for Example 1B in Example 1C.

EXAMPLE 29C 5-bromo-N'-((4-bromophenyl)methylidene)-3-phenyl-1H-indole-2-carbohydrazide The desired product was prepared by substituting Example 29B for Example 1C in Example 2.

MS (ESI(+)) m/e 498 (M+H)$^+$; $^1$H NMR (300 MHz, DMSO-d$_6$) δ 7.15–7.56 (m, 9H), 7.59–7.77 (br m, 3H), 8.07 (br s, 1H).

EXAMPLE 30

5-bromo-N'-((4-chlorophenyl)methylidene)-3-phenyl-1H-indole-2-carbohydrazide

The desired product was prepared by substituting Example 29B and 4-chlorobenzaldehyde for Example 1C and 4-bromobenzaldehyde, respectively, in Example 2.

MS (ESI(+)) m/e 454 (M+H)$^+$; $^1$H NMR (300 MHz, DMSO-d$_6$) δ 7.25–7.57 (m, 9H), 7.66–7.77 (br s, 3H), 8.07 (br s, 1H).

EXAMPLE 31

5-bromo-N'-((4-fluorophenyl)methylidene)-3-phenyl-1H-indole-2-carbohydrazide

The desired product was prepared by substituting Example 29B and 4-fluorobenzaldehyde for Example 1C and 4-bromobenzaldehyde, respectively, in Example 2.

MS (ESI(−)) m/e 436(M+H)$^-$; $^1$H NMR (300 MHz, DMSO-d$_6$) δ 7.07–7.57 (m, 9H), 7.74 (br s, 3H), 8.08 (br s, 1H).

EXAMPLE 32

N'-((4-cyanophenyl)methylidene)-3-isopropyl-1H-indole-2-carbohydrazide

The desired product was prepared by substituting Example 20C and 4-cyanobenzaldehyde for Example 1C and 4-bromobenzaldehyde, respectively, in Example 2.

MS (ESI(−)) m/e 329(M−H)$^-$; $^1$H NMR (300 MHz, DMSO-d$_6$) δ 1.40 (d, 6H), 3.83 (br m, 1H), 7.01–7.07 (dt, 1H), 7.18–7.26 (dt, 1H), 7.44 (d, 1H), 7.81 (d, 1H), 7.91 (s, 4H), 8.37 (br s, 1H).

EXAMPLE 33

N'-((4-cyanophenyl)methylidene)-5-fluoro-3-phenyl-1H-indole-2-carbohydrazide

The desired product was prepared by substituting Example 23B and 4-cyanobenzaldehyde for Example 1C and 4-bromobenzaldehyde, respectively, in Example 2.

MS (ESI(+)) m/e 383 (M+H)+; 1H NMR (300 MHz, DMSO-d6) δ 7.13–7.22 (m, 1H), 7.24–7.60 (m, 7H), 7.68–8.22 (m, 5H).

EXAMPLE 34

N'-((4-cyanophenyl)methylidene)-5-methoxy-3-phenyl-1H-indole-2-carbohydrazide

The desired product was prepared by substituting Example 26B and 4-cyanobenzaldehyde for Example 1C and 4-bromobenzaldehyde, respectively, in Example 2.

MS (ESI(+)) m/e 395 (M+H)+; 1H NMR (300 MHz, DMSO-d6) δ 3.75 (s, 3H), 6.93–6.97 (m, 1H), 7.04 (m, 1H), 7.22–7.56 (m, 6H), 7.60–7.95 (m, 4H), 8.07 (br s, 1H).

EXAMPLE 35

5-bromo-N'-((4-cyanophenyl)methylidene)-3-phenyl-1H-indole-2-carbohydrazide

The desired product was prepared by substituting Example 29B and 4-cyanobenzaldehyde for Example 1C and 4-bromobenzaldehyde, respectively, in Example 2.

MS (ESI(–)) m/e 443 (M–H)–; 1H NMR (300 MHz, DMSO-d6) δ 7.28–7.56 (m, 8H), 7.73 (br s, 1H), 7.78–7.94 (br m, 3H), 8.15 (br s, 1H).

EXAMPLE 36

3-isopropyl-N'-(phenylmethylidene)-1H-indole-2-carbohydrazide

The desired product was prepared by substituting Example 20C and benzaldehyde for Example 1C and 4-bromobenzaldehyde, respectively, in Example 2.

MS (ESI(–)) m/e 304 (M–H)–; 1H NMR (300 MHz, DMSO-d6) δ 1.40 (d, 6H), 3.83 (br m, 1H), 7.01–7.07 (dt, 1H), 7.18–7.25 (dt, 1H), 7.40–7.50 (m, 4H), 7.68–7.77 (br m, 2H), 7.81 (d, 1H) 8.33 (br s, 1H).

EXAMPLE 37

5-fluoro-3-phenyl-N'-(phenylmethylidene)-1H-indole-2-carbohydrazide

The desired product was prepared by substituting Example 23B and benzaldehyde for Example 1C and 4-bromobenzaldehyde, respectively, in Example 2.

MS (ESI(+)) m/e 358 (M+H)+; 1H NMR (300 MHz, DMSO-d6) δ 7.11–7.20 (m, 1H), 7.23–7.60 (m, 11H), 7.68 (br s, 1H), 8.08 (br s, 1H).

EXAMPLE 38

5-methoxy-3-phenyl-N'-(phenylmethylidene)-1H-indole-2-carbohydrazide

The desired product was prepared by substituting Example 26B and benzaldehyde for Example 1C and 4-bromobenzaldehyde, respectively, in Example 2.

MS (ESI(+)) m/e 370 (M+H)+; 1H NMR (300 MHz, DMSO-d6) δ 3.75 (s, 3H), 6.93–6.97 (m, 1H), 7.04 (s, 1H), 7.22–7.55 (m, 9H), 7.58–7.73 (m, 2H), 8.05 (br s, 1H).

EXAMPLE 39

5-bromo-3-phenyl-N'-(phenylmethylidene)-1H-indole-2-carbohydrazide

The desired product was prepared by substituting Example 29B and benzaldehyde for Example 1C and 4-bromobenzaldehyde, respectively, in Example 2.

MS (ESI(+)) m/e 420 (M+H)+; 1H NMR (300 MHz, DMSO-d6) δ 7.26–7.62 (m, 10H), 7.82–7.82 (m, 3H), 8.08 (br s, 1H).

EXAMPLE 40

3-isopropyl-N'-((4-nitrophenyl)methylidene)-1H-indole-2-carbohydrazide

The desired product was prepared by substituting Example 20C and 4-nitrobenzaldehyde for Example 1C and 4-bromobenzaldehyde, respectively, in Example 2.

MS (ESI(–)) m/e 349 (M–H)–; 1H NMR (300 MHz, DMSO-d6) δ 1.41 (d, 6H), 3.82 (br m, 1H), 7.01–7.07 (dt, 1H), 7.20–7.26 (dt, 1H), 7.44 (d, 1H), 7.82 (d, 1H), 7.98 (d, 2H), 8.32 (d, 2H), 8.43 (s,1H).

EXAMPLE 41

5-fluoro-N'-((4-nitrophenyl)methylidene)-3-phenyl-1H-indole-2-carbohydrazide

The desired product was prepared by substituting Example 23B and 4-nitrobenzaldehyde for Example 1C and 4-bromobenzaldehyde, respectively, in Example 2.

MS (ESI(–)) m/e 401 (M–H)–; 1H NMR (300 MHz, DMSO-d6) δ 7.13–7.22 (m, 1H), 7.25–7.57 (m, 6H), 7.85–8.40 (m, 5H).

EXAMPLE 42

5-methoxy-N'-((4-nitrophenyl)methylidene)-3-phenyl-1H-indole-2-carbohydrazide

The desired product was prepared by substituting Example 26B and 4-nitrobenzaldehyde for Example 1C and 4-bromobenzaldehyde, respectively, in Example 2.

MS (ESI(+)) m/e 415 (M+H)+; 1H NMR (300 MHz, DMSO-d6) δ 3.75 (s, 3H), 6.94–6.99 (m, 1H), 7.05 (s, 1H), 7.22–7.57 (m, 6H), 7.73–8.32 (m, 5H).

EXAMPLE 43

5-bromo-N'-((4-nitrophenyl)methylidene)-3-phenyl-1H-indole-2-carbohydrazide

The desired product was prepared by substituting Example 29B and 4-nitrobenzaldehyde for Example 1C and 4-bromobenzaldehyde, respectively, in Example 2.

MS (ESI(+)) m/e 463 (M+H)+; 1H NMR (300 MHz, DMSO-d6) δ 7.35–7.54 (m, 7H), 7.75 (br s, 1H), 7.88–8.03 (br m, 1H), 8.03–8.41 (br m, 4H).

EXAMPLE 44

N'-(1-naphthylmethylidene)-3-phenyl-1H-indole-2-carbohydrazide

The desired product was prepared by substituting 1-naphthaldehdye for 4-bromobenzaldehyde in Example 2.

MS (ESI(+)) m/e 390 (M+H)+; 1H NMR (300 MHz, DMSO-d6) δ 7.12–7.17 (m, 1H), 7.26–7.41 (m, 2H), 7.41–7.76 (m, 10H), 7.82–8.08 (br m, 3H), 8.73 (br s, 1H).

EXAMPLE 45

3-phenyl-N'-((4-(trifluoromethyl)phenyl)methylidene)-1H-indole-2-carbohydrazide

The desired product was prepared by substituting 4-(trifluoromethyl)benzaldehyde for 4-bromobenzaldehyde in Example 2.

MS (ESI(+)) m/e 408 (M+H)$^+$.

EXAMPLE 46

3-phenyl-N'-(4-quinolinylmethylidene)-1H-indole-2-carbohydrazide

The desired product was prepared by substituting 4-quinolinecarbaldehyde for 4-bromobenzaldehyde in Example 2.

MS (ESI(+)) m/e 391 (M+H)$^+$; $^1$H NMR (300 MHz, DMSO-d$_6$) δ 7.12–7.20 (m, 2H), 7.28–7.86 (m, 10H), 8.08 (br s, 1H), 8.70 (br s, 1H), 8.95 (br s, 1H).

EXAMPLE 47 methyl 4-((((3-phenyl-1H-indol-2-yl)carbonyl)hydrazono)methyl)benzoate

The desired product was prepared by substituting ethyl 4-formylbenzoate for 4-bromobenzaldehyde in Example 2.

MS (ESI(+)) m/e 398 (M+H)$^+$; $^1$H NMR (300 MHz, DMSO-d$_6$) δ 3.87 (s, 3H), 7.11–7.16 (m, 1H), 7.27–7.35 (m, 2H) 7.38–8.17 (br m, 11H).

EXAMPLE 48

N'-((4-bromophenyl)methylidene)-3-(4-fluorophenyl)-1H-indole-2-carbohydrazide

EXAMPLE 48A ethyl 3-(4-fluorophenyl)-2-oxopropanoate

The desired product was prepared by substituting 4-fluorobenzylmagnesium bromide for benzylmagnesium chloride in Example 1A.

EXAMPLE 48B ethyl 3-(4-fluorophenyl)-1H-indole-2-carboxylate

The desired product was prepared by substituting Example 48A for Example 1A in Example 1B, collecting the resulting precipitate by filtration, washing the solid with ethanol, and drying under vacuum.

EXAMPLE 48C 3-(4-fluorophenyl)-1H-indole-2-carbohydrazide

The desired product was prepared by substituting Example 48B for Example 1B in Example 1C.

EXAMPLE 48D

N'-((4-bromophenyl)methylidene)-3-(4-fluorophenyl)-1H-indole-2-carbohydrazide

The desired product was prepared by substituting Example 48C for Example 1C in Example 2.

MS (ESI(+)) m/e 438 (M+H)$^+$; $^1$H NMR (300 MHz, DMSO-d$_6$) δ 7.11–7.17 (m, 1H), 7.19–7.35 (m, 3H), 7.48–7.73 (m, 7H), 8.10 (br s, 1H).

EXAMPLE 49

N'-((4-chlorophenyl)methylidene)-3-(4-fluorophenyl)-1H-indole-2-carbohydrazide

The desired product was prepared by substituting Example 48C and 4-chlorobenzaldehyde for Example 1C and 4-bromobenzaldehyde, respectively, in Example 2.

MS (ESI(+)) m/e 392 (M+H)$^+$; $^1$H NMR (300 MHz, DMSO-d$_6$) δ 7.12–7.17 (m, 1H), 7.19–7.35 (m, 3H), 7.38–7.65 (m, 5H), 7.66–7.81 (m, 4H), 8.11 (br s, 1H).

EXAMPLE 50

3-(4-fluorophenyl)-N'-((4-nitrophenyl)methylidene)-1H-indole-2-carbohydrazide

The desired product was prepared by substituting Example 48C and 4-nitrobenzaldehyde for Example 1C and 4-bromobenzaldehyde, respectively, in Example 2.

MS (ESI(+)) m/e 403 (M+H)$^+$; $^1$H NMR (300 MHz, DMSO-d$_6$) δ 7.12–7.17 (m, 1H), 7.19–7.35 (m, 3H), 7.48–7.57 (m, 3H), 7.76–8.35 (m, 4H), 11.64–11.98 (br m, 2H).

EXAMPLE 51

N'-((4-cyanophenyl)methylidene)-3-(4-fluorophenyl)-1H-indole-2-carbohydrazide

The desired product was prepared by substituting Example 48C and 4-cyanobenzaldehyde for Example 1C and 4-bromobenzaldehyde, respectively, in Example 2.

MS (ESI(+)) m/e 383 (M+H)$^+$; $^1$H NMR (300 MHz, DMSO-d$_6$) δ 7.12–7.17 (m, 1H), 7.19–7.33 (m, 2H), 7.48–7.57 (m, 3H), 7.62 (d, 1H), 7.74–7.96 (br m, 4H), 8.14 (br s, 1H).

EXAMPLE 52

3-(4-chlorophenyl)-N'-((4-cyanophenyl)methylidene)-1H-indole-2-carbohydrazide

EXAMPLE 52A ethyl 3-(4-chlorophenyl)-2-oxopropanoate

The desired product was prepared by substituting 4-chlorobenzylmagnesium bromide for benzylmagnesium chloride in Example 1A.

EXAMPLE 52B ethyl 3-(4-chlorophenyl)-1H-indole-2-carboxylate

A mixture of Example 52A (4.75 g, 21.0 mmol) and phenyl hydrazine (2.07 mL, 21.0 mmol) was treated with concentrated sulfuric acid (5 drops), heated to 120° C. for 15 minutes, cooled to room temperature, treated with ethanol (25 mL), treated with bubbling HCl gas for 2 minutes, and heated to reflux for 1 hour. The mixture was poured into water (30 mL) and extracted with diethyl ether. The combined extracts were washed with water and brine, dried (MgSO$_4$), filtered, and concentrated. The concentrate was recrystallized from ethanol to provide 750 mg (12%) of the desired product.

EXAMPLE 52C 3-(4-chlorophenyl)-1H-indole-2-carbohydrazide

The desired product was prepared by substituting Example 52B for Example 1B in Example 1C.

EXAMPLE 52D 3-(4-chlorophenyl)-N'-((4-cyanophenyl)methylidene)-1H-indole-2-carbohydrazide The desired product was prepared by substituting Example 52C and 4-cyanobenzaldehyde for Example 1C and 4-bromobenzaldehyde, respectively, in Example 2.

MS (ESI(+)) m/e 399(M+H)$^+$; $^1$H NMR (300 MHz, DMSO-d$_6$) δ 7.12–7.18 (m, 1H), 7.27–7.33 (m, 1H), 7.39–7.59 (m, 5H), 7.65 (d, 1H), 7.79–7.97 (m, 3H), 8.18 (br s, 1H).

EXAMPLE 53

N'-((4-bromophenyl)methylidene)-3-(4-chlorophenyl)-1H-indole-2-carbohydrazide

The desired product was prepared by substituting Example 52C for Example 1C in Example 2.

MS (ESI(–)) m/e 452 (M–H)$^-$; $^1$H NMR (300 MHz, DMSO-d$_6$) δ 7.12–7.17 (t, 1H), 7.27–7.33 (t, 1H), 7.43–7.74 (m, 10H), 8.13 (br s, 1H).

EXAMPLE 54

3-(4-chlorophenyl)-N'-((4-chlorophenyl)methylidene)-1H-indole-2-carbohydrazide

The desired product was prepared by substituting Example 52C and 4-chlorobenzaldehyde for Example 1C and 4-bromobenzaldehyde, respectively, in Example 2.

MS (ESI(–)) m/e 406 (M–H)$^-$; $^1$H NMR (300 MHz, DMSO-d$_6$) δ 7.12–7.18 (m, 1H), 7.27–7.33 (t, 1H), 7.41–7.58 (m, 8H), 7.64 (d, 1H), 7.68–7.79 (br m, 1H), 8.14 (br s, 1H).

EXAMPLE 55

3-(4-chlorophenyl)-N'-((4-nitrophenyl)methylidene)-1H-indole-2-carbohydrazide

The desired product was prepared by substituting Example 52C and 4-nitrobenzaldehyde for Example 1C and 4-bromobenzaldehyde, respectively, in Example 2.

MS (ESI(–)) m/e 417(M–H)$^-$; $^1$H NMR (300 MHz, DMSO-d$_6$) δ 7.12–7.18 (m, 1H), 7.27–7.35 (t, 1H), 7.40–7.56 (m, 8H), 7.65 (d, 1H), 7.85–8.05 (brm, 2H), 8.15–8.34 (brm, 3H).

EXAMPLE 56

N'-((4-bromo-3,5-dimethoxyphenyl)methylidene)-3-phenyl-1H-indole-2carbohydrazide The desired product was prepared by substituting 4-bromo-3,5-dimethoxybenzaldehyde for 4-bromobenzaldehyde in Example 2.

MS (ESI(–)) m/e 478 (M–H)$^-$; $^1$H NMR (300 MHz, DMSO-d$_6$) δ 3.87 (br s, 6H), 7.02 (br s, 1H), 7.09–7.17 (t, 1H), 7.25–7.56 (m, 8H), 7.65 (d, 1H), 8.05 (br s, 1H).

EXAMPLE 57

N'-((3,4-dichlorophenyl)methylidene)-3-phenyl-1H-indole-2-carbohydrazide

The desired product was prepared by substituting 3,4-dichlorobenzaldehyde for 4-bromobenzaldehyde in Example 2.

MS (ESI(+)) m/e 408 (M+H)$^+$; $^1$H NMR (300 MHz, DMSO-d$_6$) δ 7.09–7.17 (m, 1H), 7.26–7.33 (m, 1H), 7.38–8.10 (m, 10H).

EXAMPLE 58

N'-((4-bromo-2-fluorophenyl)methylidene)-3-phenyl-1H-indole-2-carbohydrazide

The desired product was prepared by substituting 4-bromo-2-fluorobenzaldehyde for 4-bromobenzaldehyde in Example 2.

MS (ESI(+)) m/e 438 (M+H)$^+$; $^1$H NMR (300 MHz, DMSO-d$_6$) δ 7.09–7.17 (m, 1H), 7.26–7.34 (t, 1H), 7.38–7.68 (m, 10H), 8.25 (br s, 1H), 11.92 (br s, 1H).

EXAMPLE 59

N'-((2,4-dichlorophenyl)methylidene)-3-phenyl-1H-indole-2-carbohydrazide

The desired product was prepared by substituting 2,4-dichlorobenzaldehyde for 4-bromobenzaldehyde in Example 2.

MS (ESI(+)) m/e 408 (M+H)$^+$; $^1$H NMR (300 MHz, DMSO-d$_6$) δ 7.09–7.17 (m, 1H), 7.26–7.34 (t, 1H), 7.38–7.56 (m, 9H), 7.63–7.68 (d, 1H), 8.45 (br s, 1H), 11.92 (br s, 1H).

EXAMPLE 60

N'-((4-chloro-3-nitrophenyl)methylidene)-3-phenyl-1H-indole-2-carbohydrazide

The desired product was prepared by substituting 4-chloro-3-nitrobenzaldehyde for 4-bromobenzaldehyde in Example 2.

MS (ESI(–)) m/e 417 (M–H)$^-$; $^1$H NMR (300 MHz, DMSO-d$_6$) δ 7.10–7.17 (m, 1H), 7.26–7.35 (t, 1H), 7.37–8.40 (m, 10H), 8.13 (br s, 1H), 11.92 (br s, 1H).

EXAMPLE 61

N'-((4-fluorophenyl)methylidene)-3-methyl-1H-indole-2-carbohydrazide

EXAMPLE 61A ethyl 2-oxobutanoate

The desired product was prepared by substituting ethylmagnesium bromide for benzylmagnesium chloride in Example 1A.

EXAMPLE 61B ethyl 3-methyl-1H-indole-2-carboxylate

The desired product was prepared by substituting Example 61A for Example 1A in Example 1B, then purifying the resulting product by flash column chromatography on silica gel with 0–10% ethyl acetate/hexanes. $^1$H NMR (300 MHz, DMSO-d$_6$) δ 1.36 (t, 3H), 2.54 (s, 3H), 4.34 (q, 2H), 7.05 (t, 1H), 7.25 (t, 1H), 7.40 (d, 1H), 7.64 (d, 1H), 11.44 (s, 1H).

EXAMPLE 61C 3-methyl-1H-indole-2-carbohydrazide

The desired product was prepared by substituting Example 61B for Example 1B in Example 1C, then purifying the resulting product by flash column chromatography on silica gel with 0–20% ethyl acetate/hexanes.

MS (ESI(+)) m/e 190 (M+H)$^+$; $^1$H NMR (300 MHz, DMSO-d$_6$) δ 2.47 (s, 3H), 4.49 (s, 2H), 7.03 (t, 1H), 7.18 (t, 1H), 7.36 (d, 1H), 7.58 (d, 1H), 9.12 (s, 1H), 11.07 (s, 1H).

EXAMPLE 61D

N'-((4-fluorophenyl)methylidene)-3-methyl-1H-indole-2-carbohydrazide

The desired product was prepared by substituting Example 61C and 4-fluorobenzaldehyde for Example 1C and 4-bromobenzaldehyde, respectively, in Example 2.

MS (ESI(+)) m/e 296 (M+H)+; 1H NMR (300 MHz, DMSO-d6) δ 2.54 (s, 3H), 7.70 (t, 1H), 7.22–7.35 (m, 3H), 7.43 (d, 1H), 7.64 (d, 1H), 7.80 (m, 2H), 8.36 (br s, 1H).

EXAMPLE 62

N'-((4-cyanophenyl)methylidene)-3-(3,4-dimethylphenyl)-1H-indole-2-carbohydrazide

EXAMPLE 62A ethyl 3-(3,4-dimethylphenyl)-2-oxopropanoate

The desired product was prepared by substituting 3,4-dimethylbenzylmagnesium bromide for benzylmagnesium chloride in Example 1A.

EXAMPLE 62B ethyl 3-(3,4-dimethylphenyl)-1H-indole-2-carboxylate

The desired product was prepared by substituting Example 62A for Example 1A in Example 1B, then purifying the resulting product by flash column chromatography on silica gel with 0–10% ethyl acetate/hexanes.

MS (ESI(−)) m/e 292 (M−H)−; 1H NMR (300 MHz, DMSO-d6) δ 1.20 (t, 3H), 2.28 (s, 6H), 4.22 (q, 2H), 7.07 (t, 1H), 7.20 (s, 2H), 7.27 (s, 1H), 7.29 (t, 1H), 7.48 (d, 2H), 11.81 (s, 1H).

EXAMPLE 62C 3-(3,4-dimethylphenyl)-1H-indole-2-carbohydrazide

The desired product was prepared by substituting Example 62B for Example 1B in Example 1C, then purifying the resulting product by recrystallization from ethanol.

EXAMPLE 62D

N'-((4-cyanophenl)methylidene)-3-(3,4-dimethylphenyl)-1H-indole-2-carbohydrazide The desired product was prepared by substituting Example 62C and 4-cyanobenzaldehyde for Example 1C and 4-bromobenzaldehyde in Example 2.

MS (ESI(+)) m/e 393 (M+H)+; 1H NMR (300 MHz, DMSO-d6) δ 2.22 (br s, 6H), 7.08–7.18 (m, 3H), 7.25–7.31 (m, 3H), 7.49 (d, 1H), 7.61 (d, 1H), 7.85 (br s, 3H), 8.08 (br s, 1H).

EXAMPLE 63

N'-((4-chlorophenyl)methylidene)-3-(3,4-dimethylphenyl)-1H-indole-2-carbohydrazide The desired product was prepared by substituting Example 62C and 4-chlorobenzaldehyde for Example 1C and 4-bromobenzaldehyde in Example 2.

MS (ESI(+)) m/e 402 (M+H)+; 1H NMR (300 MHz, DMSO-d6) δ 2.25 (br s, 6H), 7.10 (t, 1H), 7.20 (br s, 2H), 7.24–7.32 (m, 3H), 7.48 (m, 3H), 7.60 (d, 1H), 7.68 (br s, 1H), 8.04 (br s, 1H).

EXAMPLE 64

3-(3,4-dimethylphenyl)-N'-((4-nitrophenyl)methylidene)-1H-indole-2-carbohydrazide The desired product was prepared by substituting Example 62C and 4-nitrobenzaldehyde for Example 1C and 4-bromobenzaldehyde in Example 2.

MS (ESI(+)) m/e 413 (M+H)+; 1H NMR (300 MHz, DMSO-d6) δ 2.22 (br s, 6H), 7.12 (t, 2H), 7.19 (br s, 2H), 7.26–7.32 (m, 2H), 7.50 (d, 1H), 7.63 (d, 1H), 7.90 (br s, 1H), 8.02 (br s, 1H), 8.25 (m, 2H).

EXAMPLE 65

3-(3,4-dimethylphenyl)-N'-((4-fluorophenyl)methylidene)-1H-indole-2-carbohydrazide The desired product was prepared by substituting Example 62C and 4-fluorobenzaldehyde for Example 1C and 4-bromobenzaldehyde, respectively, in Example 2.

MS (ESI(+)) m/e 386 (M+H)+; 1H NMR (300 MHz, DMSO-d6) δ 2.28 (br s, 6H), 7.10 (t, 1H), 7.20–7.32 (m, 6H), 7.49 (d, 1H), 7.61 (d, 1H), 7.73 (br s, 1H), 8.05 (br s, 1H).

EXAMPLE 66

3-phenyl-N'-(4-pyridinylmethylidene)-1H-indole-2-carbohydrazide

The desired product was prepared by substituting isonicotinaldehyde for 4-bromobenzaldehyde in Example 2.

MS (ESI(−)) m/e 339 (M−H)−; 1H NMR (300 MHz, DMSO-d6) δ 7.10–7.17 (m, 2H), 7.26–7.33 (t, 2H), 7.35–7.68 (m, 8H), 8.03 (br s, 1H), 8.58 (br s, 2H).

EXAMPLE 67

3-phenyl-N'-(3-pyridinylmethylidene)-1H-indole-2-carbohydrazide

The desired product was prepared by substituting nicotinaldehyde for 4-bromobenzaldehyde in Example 2.

MS (ESI(+)) m/e 341 (M+H)+; 1H NMR (300 MHz, DMSO-d6) δ 7.09–7.17 (m, 2H), 7.24–7.57 (m, 10H), 7.61 (d, 1H), 8.13 (br s, 1H), 8.58 (br s, 1H).

EXAMPLE 68

3-phenyl-N'-(2-pyridinylmethylidene)-1H-indole-2-carbohydrazide

The desired product was prepared by substituting 2-pyridinecarbaldehyde for 4-bromobenzaldehyde in Example 2.

MS (ESI(+)) m/e 341 (M+H)+; 1H NMR (300 MHz, DMSO-d6) δ 7.11–7.18 (m, 2H), 7.26–7.61 (m, 10H), 7.65 (d, 1H), 8.03 (br s, 1H), 8.57 (br s, 1H).

EXAMPLE 69

N'-((6-methyl-2-pyridinyl)methylidene)-3-phenyl-1H-indole-2-carbohydrazide

The desired product was prepared by substituting 6-methyl-2-pyridinecarbaldehyde for 4-bromobenzaldehyde in Example 2.

MS (ESI(+)) m/e 355 (M+H)+; 1H NMR (300 MHz, DMSO-d6) δ 2.46 (s, 3H), 7.09–7.17 (m, 2H), 7.22–7.40 (m, 4H) 7.42–7.57 (m, 4H), 7.63–7.79 (m, 2H), 8.01 (br s, 1H).

EXAMPLE 70

3-methyl-N'-(phenylmethylidene)-1H-indole-2-carbohydrazide

The desired product was prepared by substituting Example 61C and benzaldehyde for Example 1C and 4-bromobenzaldehyde, respectively, in Example 2.

EXAMPLE 71

N'-((4-bromophenyl)methylidene)-3-methyl-1H-indole-2-carbohydrazide

The desired product was prepared by substituting Example 61C for Example 1C in Example 2.

EXAMPLE 72

N'-((4-cyanophenl)methylidene)-3-methyl-1H-indole-2-carbohydrazide

The desired product was prepared by substituting Example 61C and 4-cyanobenzaldehyde for Example 1C and 4-bromobenzaldehyde, respectively, in Example 2.

EXAMPLE 73

N'-(3-furylmethylidene)-3-phenyl-1H-indole-2-carbohydrazide

The desired product was prepared by substituting 3-furaldehyde for 4-bromobenzaldehyde in Example 2.

MS (ESI(+)) m/e 330 (M+H)$^+$; $^1$H NMR (300 MHz, DMSO-d$_6$) δ 6.78 (br s, 1H), 7.12 (t, 1H), 7.24–7.36 (m, 3H), 7.41–7.55 (m, 4H), 7.63 (d, 1H), 7.75 (br s, 1H), 8.02 (s, 1H), 8.12 (s, 1H).

EXAMPLE 74

N'-((5-methyl-2-furyl)methylidene)-3-phenyl-1H-indole-2-carbohydrazide

The desired product was prepared by substituting 5-methyl-2-furaldehyde for 4-bromobenzaldehyde in Example 2.

MS (ESI(+)) m/e 344 (M+H)$^+$; $^1$H NMR (300 MHz, DMSO-d$_6$) δ 2.33 (s, 3H), 6.24 (s, 1H), 6.77 (s, 1H), 7.13 (t, 1H), 7.24–7.55 (m, 7H), 7.64 (d, 1H), 7.84 (br s, 1H).

EXAMPLE 75

N'-(1-benzofuran-2-ylmethylidene)-3-phenyl-1H-indole-2-carbohydrazide

The desired product was prepared by substituting 1-benzofuran-2-carbaldehyde for 4-bromobenzaldehyde in Example 2.

MS (ESI(+)) m/e 380 (M+H)$^+$; $^1$H NMR (300 MHz, DMSO-d$_6$) δ 7.11–7.17 (t, 2H), 7.24–7.55 (m, 10H), 7.61–7.72 (d, 4H), 8.08 (br s, 1H).

EXAMPLE 76

N'-((5-nitro-2-furyl)methylidene)-3-phenyl-1H-indole-2-carbohydrazide

The desired product was prepared by substituting 5-nitro-2-furaldehyde for 4-bromobenzaldehyde in Example 2.

MS (ESI(-)) m/e 373 (M–H)$^-$; $^1$H NMR (300 MHz, DMSO-d$_6$) δ 7.13 (t, 1H), 7.28–7.35 (m, 2H), 7.37–7.55 (m, 4H) 7.65 (d, 1H), 7.76 (s, 1H), 7.97 (br s, 1H).

EXAMPLE 77

N'-(2-furylmethylidene)-3-phenyl-1H-indole-2-carbohydrazide

The desired product was prepared by substituting 2-furaldehyde for 4-bromobenzaldehyde in Example 2.

MS (ESI(+)) m/e 330 (M+H)$^+$; $^1$H NMR (300 MHz, DMSO-d$_6$) δ 6.62 (br s, 1H), 6.90 (br s, IH), 7.12 (t, 1H), 7.247.37 (m, 3H), 7.39–7.55 (m, 4H), 7.64 (d, 1H), 7.83 (s, 1H), 7.94 (s, 1H).

EXAMPLE 78

3-isopropyl-N'-((5-nitro-2-furyl)methylidene)-1H-indole-2-carbohydrazide

The desired product was prepared by substituting Example 20C and 5-nitro-2-furaldehyde for Example 1C and 4-bromobenzaldehyde, respectively, in Example 2.

MS (ESI(–) m/e 339 (M–H)$^-$; $^1$H NMR (300 MHz, DMSO-d$_6$) δ 1.41 (d, 6H), 3.80 (m, 1H), 7.02–7.07 (m, 1H), 7.20–7.29 (m, 2H), 7.43 (d, 1H), 7.79–7.85 (m, 2H), 8.27 (s, 1H).

EXAMPLE 79

3-isopropyl-N'-((5-methyl-2-furyl)methylidene)-1H-indole-2-carbohydrazide

The desired product was prepared by substituting Example 20C and 5-methyl2-furaldehyde for Example 1C and 4-bromobenzaldehyde, respectively, in Example 2.

MS (ESI(+)) m/e 310 (M+H)$^+$; $^1$H NMR (300 MHz, DMSO-d$_6$) δ 1.40 (d, 6H), 2.36 (s, 3H), 3.78 (br m, 1H), 6.27 (m, 1H), 6.81 (d, 1H), 6.97–7.06 (m, 1H), 7.16–7.23 (m, 1H), 7.41 (d, 1H), 7.28 (d, 1H), 8.10 (br s, 1H).

EXAMPLE 80

3-isopropyl-N'-(3-pyridinylmethylidene)-1H-indole-2-carbohydrazide

The desired product was prepared by substituting Example 20C and nicotinaldehyde for Example 1C and 4-bromobenzaldehyde, respectively, in Example 2.

MS (ESI(+)) m/e 307 (M+H)$^+$; $^1$H NMR (300 MHz, DMSO-d$_6$) δ 1.41 (d, 6H), 3.83 (br m, 1H), 7.00–7.06 (m, 1H) 7.18–7.25 (m, 1H), 7.40–7.53 (m, 2H), 7.80 (d, 1H), 8.13 (m, 1H), 8.36 (br s, 1H), 8.62 (m, 1H), 8.87 (d, 1H).

EXAMPLE 81

N'-(2-furylmethylidene)-3-isopropyl-1H-indole-2-carbohydrazide

The desired product was prepared by substituting Example 20C and 2-furaldehyde for Example 1C and 4-bromobenzaldehyde, respectively, in Example 2.

MS (ESI(+)) m/e 296 (M+H)$^+$; $^1$H NMR (300 MHz, DMSO-d$_6$) δ 1.40 (d, 6H), 3.79 (br s, 1H), 6.65 (m, 1H), 6.94 (d, 1H), 7.00–7.06 (m, 1H), 7.16–7.23 (m, 1H), 7.42 (d, 1H), 7.78 (d, 1H), 7.85 (s, 1H), 8.20 (br s, 1H).

EXAMPLE 82

3-methyl-N'-((5-nitro-2-furyl)methylidene)-1H-indole-2-carbohydrazide

The desired product was prepared by substituting Example 61C and 5-nitro-2-furaldehyde for Example 1C and 4-bromobenzaldehyde, respectively, in Example 2.

MS (ESI(–)) m/e 311 (M–H)$^-$; $^1$H NMR (300 MHz, DMSO-d$_6$) δ 2.54 (s, 3H), 7.05–7.12 (m, 1H), 7.23–7.29 (m, 1H) 7.43 (d, 1H), 7.66 (d, 1H), 7.81 (d, 1H), 8.31 (s, 1H).

EXAMPLE 83

3-methyl-N'-((5-methyl-2-furyl)methylidene)-1H-indole-2-carbohydrazide

The desired product was prepared by substituting Example 61C and 5-methyl-2-furaldehyde for Example 1C and 4-bromobenzaldehyde, respectively, in Example 2.

MS (ESI(+)) m/e 282 (M+H)$^+$; $^1$H NMR (300 MHz, DMSO-d$_6$) δ 2.36 (s, 3H), 2.53 (s, 3H), 6.28 (m, 1H), 6.83 (d, 1H), 7.04–7.10 (m, 1H), 7.20–7.27 (m, 1H), 7.42 (d, 1H), 7.63 (d, 1H), 8.14 (br s, 1H),

EXAMPLE 84

3-methyl-N'-(3-pyridinylmethylidene)-1H-indole-2-carbohydrazide

The desired product was prepared by substituting Example 61C and nicotinaldehyde for Example 1C and 4-bromobenzaldehyde, respectively, in Example 2.

MS (ESI(+)) m/e 279 (M+H)$^+$; $^1$H NMR (300 MHz, DMSO-d$_6$) δ 2.53 (s, 3H), 6.65 (m, 1H), 7.05–7.11 (m, 1H), 7.22–7.28 (m, 1H), 7.42–7.53 (m, 2H), 7.65 (d, 1H), 8.15 (m, 1H), 8.40 (br s, 1H), 8.62 (m, 1H), 8.88 (d, 1H).

EXAMPLE 85

N'-(2-furylmethylidene)-3-methyl-1H-indole-2-carbohydrazide

The desired product was prepared by substituting Example 61C and 2-furaldehyde for Example 1C and 4-bromobenzaldehyde, respectively, in Example 2.

MS (ESI(+)) m/e 268 (M+H)$^+$; $^1$H NMR (300 MHz, DMSO-d$_6$) δ 2.53 (s, 3H), 6.65 (m, 1H), 6.95 (d, 1H), 7.04–7.10 (m, 1H), 7.21–7.27 (m, 1H), 7.43 (d, 1H), 7.63 (d, 1H), 7.86 (m, 1H), 8.24 (br s, 1H).

EXAMPLE 86

3-phenyl-N'-(1,3-thiazol-2-ylmethylidene)-1H-indole-2-carbohydrazide

The desired product was prepared by substituting 1,3-thiazole-2-carbaldehyde for 4-bromobenzaldehyde in Example 2.

MS (ESI(−)) m/e 345 (M−H)$^-$; $^1$H NMR (300 MHz, DMSO-d$_6$) δ 7.10–7.17 (m, 1H), 7.26–7.36 (m, 2H), 7.38–7.57 (m, 4H), 7.65 (d, 1H), 7.83 (br s, 1H), 7.93 (s, 1H), 8.27 (br s, 1H).

EXAMPLE 87

N'-((4,5-dimethyl-2-furyl)methylidene)-3-phenyl-1H-indole-2-carbohydrazide

The desired product was prepared by substituting 4,5-dimethyl-2-furaldehyde for 4-bromobenzaldehyde in Example 2.

MS (ESI(+)) m/e 358 (M+H)$^+$; $^1$H NMR (300 MHz, DMSO-d$_6$) δ 1.93 (s, 3H), 2.25 (s, 3H), 6.68 (s, 1H), 7.08–7.15 (m, 1H), 7.24–7.38 (m, 2H), 7.40–7.54 (m, 4H), 7.64 (d, 1H), 7.78 (s, 1H).

EXAMPLE 88

N'-((5-(4-chlorophenyl)-2-furyl)methylidene)-3-phenyl-1H-indole-2-carbohydrazide The desired product was prepared by substituting 5-(4-chlorophenyl)-2-furaldehyde for 4-bromobenzaldehyde in Example 2.

MS (ESI(+)) m/e 440 (M+H)$^+$; $^1$H NMR (300 MHz, DMSO-d$_6$) δ 7.03 (br s, 1H), 7.10–7.20 (m, 2H), 7.26–7.49 (m, 3H), 7.40–7.57 (m, 6H), 7.65 (d, 1H), 7.76–7.86 (br m, 2H), 7.98 (br s, 1H).

EXAMPLE 89

N'-((5-ethyl-2-furyl)methylidene)-3-phenyl-1H-indole-2-carbohydrazide

The desired product was prepared by substituting 5-ethyl-2-furaldehyde for 4-bromobenzaldehyde in Example 2.

MS (ESI(+)) m/e 358 (M+H)$^+$; $^1$H NMR (300 MHz, DMSO-d$_6$) δ 1.19 (t, 3H), 2.68 (br q, 2H), 6.25 (br s, 1H), 6.78 (br s, 1H), 7.09–7.16 (m, 1H), 7.24–7.38 (m, 2H), 7.40–7.56 (m, 5H), 7.63 (d, 1H), 7.85 (br s, 1H).

EXAMPLE 90

(5-((2-((3-phenyl-1H-indol-2-yl)carbonyl)hydrazono)methyl)-2-furyl)methyl acetate The desired product was prepared by substituting (5-formyl-2-furyl)methyl acetate for 4-bromobenzaldehyde in Example 2.

MS (ESI(−)) m/e 400 (M−H)$^-$; $^1$H NMR (300 MHz, DMSO-d$_6$) δ 2.06 (s, 3H), 5.06 (s, 2H), 6.65 (br s, 1H), 6.87 (br s, 1H), 7.09–7.16 (m, 1H), 7.25–7.39 (m, 2H), 7.39–7.56 (m, 5H), 7.65 (d, 1H), 7.90 (br s, 1H).

EXAMPLE 91

N'-((5-(4-nitrophenyl)-2-furyl)methylidene)-3-phenyl-1H-indole-2-carbohydrazide

The desired product was prepared by substituting 5-(4-nitrophenyl)-2-furaldehyde for 4-bromobenzaldehyde in Example 2.

MS (ESI(−)) m/e 449 (M−H)$^-$; $^1$H NMR (300 MHz, DMSO-d$_6$) δ 7.10–8.37 (m, 15H).

EXAMPLE 92

N'-((4-methyl-1H-imidazol-5-yl)methylidene)-3-phenyl-1H-indole-2-carbohydrazide

The desired product was prepared by substituting 4-methyl-1H-imidazole-5-carbaldehyde for 4-bromobenzaldehyde in Example 2.

MS (ESI(+)) m/e 344 (M+H)$^+$; $_1$H NMR (300 MHz, DMSO-d$_6$) δ 2.26 (s, 3H), 7.05–7.13 (m, 1H), 7.16–7.33 (m, 4H) 7.35–7.46 (m, 2H), 7.46–7.57 (m, 4H).

EXAMPLE 93

N'-(1H-imidazol-2-ylmethylidene)-3-phenyl-1H-indole-2-carbohydrazide

The desired product was prepared by substituting 1H-imidazole-2-carbaldehyde for 4-bromobenzaldehyde in Example 2.

MS (ESI(+)) m/e 330 (M+H)$^+$; $^1$H NMR (300 MHz, DMSO-d$_6$) δ 6.76 (s, 1H), 7.03–7.34 (m, 5H), 7.37–7.56 (m, 5H 7.64 (d, 1H), 7.96 (br s, 1H).

EXAMPLE 94

N'-((1-methyl-1H-imidazol-2-yl)methylidene)-3-phenyl-1H-indole-2-carbohydrazide

The desired product was prepared by substituting 1-methyl-1H-imidazole-2-carbaldehyde for 4-bromobenzaldehyde in Example 2.

MS (ESI(+)) m/e 344 (M+H)$^+$; $^1$H NMR (300 MHz, DMSO-d$_6$) δ 3.95 (br d, 1H), 4.45 (br s, 1H), 7.02–7.66 (m, 9H), 8.05 (s, 1H), 8.75 (br s, 1H).

EXAMPLE 95

N'-(1H-imidazol-5-ylmethylidene)-3-phenyl-1H-indole-2-carbohydrazide

The desired product was prepared by substituting 1H-imidazole-5-carbaldehyde for 4-bromobenzaldehyde in Example 2.

MS (ESI(+)) m/e 330 (M+H)$^+$; $^1$H NMR (300 MHz, DMSO-d$_6$) δ 4.03 (s, 1H), 4.45 (br d, 1H), 7.05–7.57 (m, 9H), 8.75 (br s, 1H).

EXAMPLE 96

N'-((2-chloro-3-quinolinyl)methylidene)-3-phenyl-1H-indole-2-carbohydrazide

The desired product was prepared by substituting 2-chloro-3-quinolinecarbaldehyde for 4-bromobenzaldehyde in Example 2.

MS (ESI(+)) m/e 425 (M+H)$^+$; $^1$H NMR (300 MHz, DMSO-d$_6$) δ 7.12–7.18 (m, 1H), 7.27–7.35 (m, 1H), 7.36–7.50 (br m, 2H), 7.51–7.60 (m, 3H), 7.65–7.73 (m, 2H), 7.82–7.89 (m, 1H), 7.93–8.00 (m, 1H), 8.21 (br s, 1H), 8.55 (br s, 1H), 8.96 (br s, 1H).

EXAMPLE 97

3-phenyl-N'-(1H-pyrrol-2-ylmethylidene)-1H-indole-2-carbohydrazide

The desired product was prepared by substituting 1H-pyrrole-2-carbaldehyde for 4-bromobenzaldehyde in Example 2.

MS (ESI(+)) m/e 329 (M+H)$^+$; $^1$H NMR (300 MHz, DMSO-d$_6$) δ 6.12 (br d, 1H), 6.44 (br d, 1H), 6.90 (br d, 1H), 7.07–7.14 (m, 1H), 7.24–7.38 (m, 3H), 7.42–7.57 (m, 6H), 7.64 (d, 1H), 7.88 (s, 1H).

EXAMPLE 98

N'-((1-methyl-1H-pyrrol-2-yl)methylidene)-3-phenyl-1H-indole-2-carbohydrazide

The desired product was prepared by substituting 1-methyl-1H-pyrrole-2-carbaldehyde for 4-bromobenzaldehyde in Example 2.

MS (ESI(+)) m/e 343 (M+H)$^+$; $^1$H NMR (300 MHz, DMSO-d$_6$) δ 3.84 (s, 3H), 6.08 (br d, 1H), 6.45 (br d, 1H), 6.94 (br d, H), 7.04–7.14 (m, 1H), 7.20–7.38 (m, 3H), 7.42–7.57 (m, 6H), 7.63 (d, 1H), 7.99 (s, 1H).

EXAMPLE 99

N'-((4-chloro-1-methyl-1H-pyrazol-3-yl)methylidene)-3-phenyl-1H-indole-2-carbohydrazide The desired product was prepared by substituting 4-chloro-1-methyl-1H-pyrazole-3-carbaldehyde for 4-bromobenzaldehyde in Example 2.

MS (ESI(+)) m/e 378 (M+H)$^+$; $^1$H NMR (300 MHz, DMSO-d$_6$) δ 3.63 (s, 3H), 7.09–7.57 (m, 9H), 7.63 (d, 1H), 8.02 (s, 1H).

EXAMPLE 100

N'-((4-(difluoromethoxy)phenyl)methylidene)-3-methyl-1H-indole-2-carbohydrazide

The desired product was prepared by substituting Example 61C and 4-(difluoromethoxy)benzaldehyde for Example 1C and 4-bromobenzaldehyde, respectively, in Example 2.

MS (ESI(+)) m/e 344 (M+H)$^+$; $^1$H NMR (300 MHz, DMSO-d$_6$) δ 2.52 (s, 3H), 7.07 (t, 1H), 7.25 (t, 1H), 7.27 (d, 2H), 7.08–7.58 (t, 1H), 7.44 (d, 1H), 7.64 (d, 1H), 7.80 (d, 2H), 8.34 (s, 1H), 11.28 (s, 1H), 11.48 (s, 1H).

Following Scheme 1 and the examples above, the following compounds can be prepared:

EXAMPLE 101

4-((((3-isopropyl-1H-indol-2-yl)carbonyl)hydrazono)methyl)benzamide

EXAMPLE 102

N'-((4-fluorophenyl)methylidene)-3-vinyl-1H-indole-2-carbohydrazide

EXAMPLE 103

4-((((3-phenyl-1H-indol-2-yl)carbonyl)hydrazono)methyl)benzenesulfonamide

EXAMPLE 104

N'-((4-hydroxyphenyl)methylidene)-3-phenyl-1H-indole-2-carbohydrazide

EXAMPLE 105

4-((((3-phenyl-1H-indol-2-yl)carbonyl)hydrazono)methyl)phenyl sulfamate

EXAMPLE 106

N'-((3-chloro-5-(trifluoromethyl)-2-pyridinyl)methylidene)-3-phenyl-1H-indole-2-carbohydrazide

EXAMPLE 107

N'-((4-chloro-13-thiazol-2-yl)methylidene)-3-isopropyl-1H-indole-2-carbohydrazide

EXAMPLE 108

3-isopropyl-N'-(3-thienylmethyidene)-1H-indole-2-carbohydrazide

EXAMPLE 109

3-isopropyl-N'-(2-thienylmethylidene)-1H-indole-2-carbohydrazide

EXAMPLE 110

3-isopropyl-N'-((3-methyl-2-thienyl)methylidene)-1H-indole-2-carbohydrazide

EXAMPLE 111

N'-((5-chloro-2-thienyl)methylidene)-3-isopropyl-1H-indole-2-carbohydrazide

EXAMPLE 112

N'-(1-benzofuran-2-ylmethylidene)-3-isopropyl-1H-indole-2-carbohydrazide

It will be evident to one skilled in the art that the instant invention is not limited to the forgoing illustrative examples, and that it can be embodied in other specific forms without

What is claimed is:

1. A compound of formula (I),

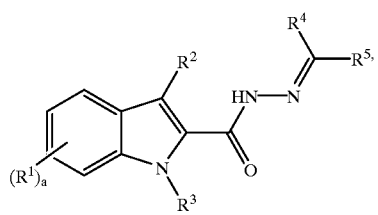

or a therapeutically acceptable salt thereof, wherein
a is 0, 1, 2, 3, or 4;
each $R^1$ is independently selected from the group consisting of alkoxy, amino, halo, hydroxy and nitro;
$R^2$ is selected from the group consisting of alkenyl, alkyl, alkynyl, aryl, and heterocycle;
$R^3$ is selected from the group consisting of hydrogen, alkyl, and a nitrogen protecting group; and
$R^4$ and $R^5$ are independently selected from the group consisting of hydrogen, alkyl, aryl, arylalkyl, cycloalkyl, (cycloalkyl)alkyl, heterocycle, and (heterocycle)alkyl wherein the aryl, cycloalkyl and heterocycle may be optionally substituted;
with the proviso that one of $R^4$ and $R^5$ is hydrogen; and
with the proviso that when a is 1, $R^1$ is $C_1$-alkyl, $C_1$-alkoxy, halo, or nitro, $R^2$ is $C_1$-alkyl, and $R^3$ and $R^4$ are hydrogen, $R^5$ is not hydrogen, $C_3$-alkyl, $C_5$-alkyl, N-(phenyl-$C_1$-alkyl)indolyl, unsubstituted phenyl, or phenyl substituted with one member selected from the group consisting of $C_3$-alkyl, $C_1$-$C_4$-alkoxy, halo, hydroxy, and nitro; and
with the proviso that when a is 1, $R^1$ is $C_1$-alkoxy or halo, $R^2$ is unsubstituted phenyl, and $R^3$ and $R^4$ are hydrogen, $R^5$ is not hydrogen, unsubstituted indolyl, phenyl substituted with one member selected from the group consisting of $C_1$-alkoxy, $C_4$-alkoxy, halo, hydroxy, and nitro, or phenyl substituted with one hydroxy and one nitro substituent; and
with the proviso that when a is 0, $R^2$ is unsubstituted phenyl, and $R^3$ and $R^4$ are hydrogen, $R^5$ is not hydrogen or unsubstituted phenyl.

2. A compound according to claim 1 wherein $R^2$ is alkenyl.

3. A compound according to claim 2 which is N'-((4-fluorophenyl)methylidene)-3-vinyl-1H-indole-2-carbohydrazide.

4. A compound according to claim 1 wherein $R^2$ is alkyl.

5. A compound according to claim 4 wherein one of $R^4$ and $R^5$ is aryl.

6. A compound according to claim 5 selected from the group consisting of

N'-((4-methoxyphenyl)methylidene)-3-methyl-1H-indole-2-carbohydrazide,
N'-((4-bromophenyl)methylidene)-3-isopropyl-1H-indole-2-carbohydrazide,
N'-((4-chlorophenyl)methylidene)-3-isopropyl-1H-indole-2-carbohydrazide,
N'-((4-fluorophenyl)methylidene)-3-isopropyl-1H-indole-2-carbohydrazide,
N'-((4-cyanophenyl)methylidene)-3-isopropyl-1H-indole-2-carbohydrazide,
3-isopropyl-N'-(phenylmethylidene)-1H-indole-2-carbohydrazide, 3-isopropyl-N'-((4-nitrophenyl)methylidene)-1H-indole-2-carbohydrazide,
N'-((4-fluorophenyl)methylidene)-3-methyl-1H-indole-2-carbohydrazide,
3-methyl-N'-(phenylmethylidene)-1H-indole-2-carbohydrazide,
N'-((4-bromophenyl)methylidene)-3-methyl-1H-indole-2-carbohydrazide,
N'-((4-cyanophenyl)methylidene)-3-methyl-1H-indole-2-carbohydrazide,
N'-((4-(difluoromethoxy)phenyl)methylidene)-3-methyl-1H-indole-2-carbohydrazide, and
4-((((3-isopropyl-1H-indol-2-yl)carbonyl)hydrazono)methyl)benzamide.

7. A compound according to claim 4 wherein one of $R^4$ and $R^5$ is heterocycle.

8. A compound according to claim 7 wherein said heterocycle is unsubstituted.

9. A compound according to claim 8 selected from the group consisting of 3-isopropyl-N'-(3-pyridinylmethylidene)-1H-indole-2-carbohydrazide,
N'-(2-furylmethylidene)-3-isopropyl-1H-indole-2-carbohydrazide,
3-methyl-N'-(3-pyridinylmethylidene)-1H-indole-2-carbohydrazide,
N'-(2-furylmethylidene)-3-methyl-1H-indole-2-carbohydrazide,
3-isopropyl-N'-(3-thienylmethylidene)-1H-indole-2-carbohydrazide,
3-isopropyl-N'-(2-thienylmethylidene)-1H-indole-2-carbohydrazide, and
N'-(1-benzofuran-2-ylmethylidene)-3-isopropyl-1H-indole-2-carbohydrazide.

10. A compound according to claim 7 wherein said heterocycle is substituted.

11. A compound according to claim 10 selected from the group consisting of 3-isopropyl-N'-((5-nitro-2-furyl)methylidene)-1H-indole-2-carbohydrazide,
3-isopropyl-N'-((5-methyl-2-furyl)methylidene)-1H-indole-2-carbohydrazide,
3-methyl-N'-((5-nitro-2-furyl)methylidene)-1H-indole-2-carbohydrazide,
3-methyl-N'-((5-methyl-2-furyl)methylidene)-1H-indole-2-carbohydrazide,
N'-((4-chloro-1,3-thiazol-2-yl)methylidene)-3-isopropyl-1H-indole-2-carbohydrazide,
3-isopropyl-N'-((3-methyl-2-thienyl)methylidene)-1H-indole-2-carbohydrazide, and
N'-((5-chloro-2-thienyl)methylidene)-3-isopropyl-1H-indole-2-carbohydrazide.

12. A compound according to claim 1 wherein $R^2$ is aryl.

13. A compound according to claim 12 wherein one of $R^4$ and $R^5$ is alkyl.

14. A compound according to claim 13 selected from the group consisting of

N'-(butylidene)-3-phenyl-1H-indole-2-carbohydrazide, and

N'-(pentylidene)-3-phenyl-1H-indole-2-carbohydrazide.

15. A compound according to claim 12 wherein one of $R^4$ and $R^5$ is aryl.

16. A compound according to claim 15 wherein a is 1.

17. A compound according to claim 16 selected from the group consisting of

N'-((4-cyanophenyl)methylidene)-5-fluoro-3-phenyl-1H-indole-2-carbohydrazide,

N'-((4-cyanophenyl)methylidene)-5-methoxy-3-phenyl-1H-indole-2-carbohydrazide, 5-bromo-N'-((4-cyanophenyl)methylidene)-3-phenyl-1H-indole-2-carbohydrazide, 5-methoxy-3-phenyl-N'-(phenylmethylidene)-1H-indole-2-carbohydrazide, and 5-bromo-3-phenyl-N'-(phenylmethylidene)-1H-indole-2-carbohydrazide.

18. A compound according to claim 15 wherein a is 0.

19. A compound according to claim 18 wherein $R^2$ is aryl which is unsubstituted phenyl.

20. A compound according to claim 19 selected from the group consisting of

N'-((4-methoxyphenyl)methylidene)-3-phenyl-1H-indole-2-carbohydrazide,

N'-((4-bromophenyl)methylidene)-3-phenyl-1H-indole-2-carbohydrazide, 3-phenyl-N'-((4-(trifluoromethoxy)phenyl)methylidene)-1H-indole-2-carbohydrazide, N'-((4-(difluoromethoxy)phenyl)methylidene)-3-phenyl-1H-indole-2-carbohydrazide, N'-((3-bromophenyl)methylidene)-3-phenyl-1H-indole-2-carbohydrazide, N'-((4-(dihydroxyamino)phenyl)methylidene)-3-phenyl-1H-indole-2-carbohydrazide, 3-phenyl-N'-(phenylmethylidene)-1H-indole-2-carbohydrazide, N'-((3-cyanophenyl)methylidene)-3-phenyl-1H-indole-2-carbohydrazide, N'-((4-cyanophenyl)methylidene)-3-phenyl-1H-indole-2-carbohydrazide, N-(4((2-((3-phenyl-1H-indol-2-yl)carbonyl)hydrazono)methyl)phenyl)-acetamide, N'-((4-(diethylamino)phenyl)methylidene)-3-phenyl-1H-indole-2-carbohydrazide, N'-((4-isoproplyphenyl)methylidene)-3-phenyl-1H-indole-2-carbohydrazide, N'-((3-nitrophenyl)methylidene)-3-phenyl-1H-indole-2-carbohydrazide, 3-phenyl-N'-((4-(1-pyrrolidinyl)phenyl)methylidene)-1H-indole-2-carbohydrazide, N'-((4-(methylsulfonyl)phenyl)methylidene)-3-phenyl-1H-indole-2-carbohydrazide, N'-((4-chlorophenyl)methylidene)-3-phenyl-1H-indole-2-carbohydrazide, N'-(1-naphthylmethylidene)-3-phenyl-1H-indole-2-carbohydrazide, 3-phenyl-N'-((4-(trifluoromethyl)phenyl)methylidene)-1H-indole-2-carbohydrazide, methyl 4-((((3-phenyl-1H-indol-2-yl)carbonyl)hydrazono)methyl)benzoate, N'-((4-bromo-3,5-dimethoxyphenyl)methylidene)-3-phenyl-1H-indole-2-carbohydrazide, N'-((3,4-dichlorophenyl)methylidene)-3-phenyl-1H-indole-2-carbohydrazide, N'-((4-bromo-2-fluorophenyl)methylidene)-3-phenyl-1H-indole-2-carbohydrazide, N'-((2,4-dichlorophenyl)methylidene)-3-phenyl-1H-indole-2-carbohydrazide, N'-((4-chloro-3-nitrophenyl)methylidene)-3-phenyl-1H-indole-2-carbohydrazide, 4-((((3-phenyl-1H-indol-2-yl)carbonyl)hydrazono)methyl)-benzenesulfonamide, N'-((4-hydroxyphenyl)methylidene)-3-phenyl-1H-indole-2-carbohydrazide, and 4-((((3-phenyl-1H-indol-2-yl)carbonyl)hydrazono)methyl)phenyl sulfamate.

21. A compound according to claim 18 wherein $R^2$ is aryl which is substituted phenyl.

22. A compound according to claim 21 selected from the group consisting of

N'-((4-bromophenyl)methylidene)-3-(4-fluorophenyl)-1H-indole-2-carbohydrazide,

N'-((4-chlorophenyl)methylidene)-3-(4-fluorophenyl)-1H-indole-2-carbohydrazide, 3-(4-fluorophenyl)-N'-((4-nitrophenyl)methylidene)-1H-indole-2-carbohydrazide, N'-((4-cyanophenyl)methylidene)-3-(4-fluorophenyl)-1H-indole-2-carbohydrazide, 3-(4-chlorophenyl)-N'-((4-cyanophenyl)methylidene)-1H-indole-2-carbohydrazide, N'-((4-bromophenyl)methylidene)-3-(4-chlorophenyl)-1H-indole-2-carbohydrazide, 3-(4-chlorophenyl)-N'-((4-chlorophenyl)methylidene)-1H-indole-2-carbohydrazide, 3-(4-chlorophenyl)-N'-((4-nitrophenyl)methylidene)-1H-indole-2-carbohydrazide, N'-((4-cyanophenyl)methylidene)-3-(3,4-dimethylphenyl)-1H-indole-2-carbohydrazide, N'-((4-chlorophenyl)methylidene)-3-(3,4-dimethylphenyl)-1H-indole-2-carbohydrazide, 3-(3,4-dimethylphenyl)-N'-((4-nitrophenyl)methylidene)-1H-indole-2-carbohydrazide, and 3-(3,4-dimethylphenyl)-N'-((4-fluorophenyl)methylidene)-1H-indole-2-carbohydrazide.

23. A compound according to claim 12 wherein one of $R^4$ and $R^5$ is heterocycle.

24. A compound according to claim 23 wherein said heterocycle is unsubstituted.

25. A compound according to claim 24 selected from the group consisting of 3-phenyl-N'-(4-quinolinylmethylidene)-1H-indole-2-carbohydrazide, 3-phenyl-N'-(4-pyridinylmethylidene)-1H-indole-2-carbohydrazide, 3-phenyl-N'-(3-pyridinylmethylidene)-1H-indole-2-carbohydrazide, 3-phenyl-N'-(2-pyridinylmethylidene)-1H-indole-2-carbohydrazide, N'-(3-furylmethylidene)-3-phenyl-1H-indole-2-carbohydrazide, N'-(1-benzofuran-2-ylmethylidene)-3-phenyl-1H-indole-2-carbohydrazide, N'-(2-furylmethylidene)-3-phenyl-1H-indole-2-carbohydrazide, 3-phenyl-N'-(1,3-thiazol-2-ylmethylidene)-1H-indole-2-carbohydrazide, N'-(1H-imidazol-2-ylmethylidene)-3-phenyl-1H-indole-2-carbohydrazide, N'-(1H-imidazol-5-ylmethylidene)-3-phenyl-1H-indole-2-carbohydrazide, and 3-phenyl-N'-(1H-pyrrol-2-ylmethylidene)-1H-indole-2-carbohydrazide.

26. A compound according to claim 23 wherein said heterocycle is substituted.

27. A compound according to claim 26 selected from the group consisting of

N'-((6-methyl-2-pyridinyl)methylidene)-3-phenyl-1H-indole-2-carbohydrazide,

N'-((5-methyl-2-furyl)methylidene)-3-phenyl-1H-indole-2-carbohydrazide,

N'-((5-nitro-2-furyl)methylidene)-3-phenyl-1H-indole-2-carbohydrazide,

N'-((4,5-dimethyl-2-furyl)methylidene)-3-phenyl-1H-indole-2-carbohydrazide,

N'-((5-(4-methylphenyl)-2-furyl)methylidene)-3-phenyl-1H-indole-2-carbohydrazide, N'-((5-ethyl-2-furyl)methylidene)-3-phenyl-1H-indole-2-carbohydrazide, (5-((2-((3-phenyl-1H-indol-2-yl)carbonyl)hydrazono)methyl)-2-furyl)methyl acetate, N'-((5-(4-nitrophenyl)-2-furyl)methylidene)-3-phenyl-1H-indole-2-carbohydrazide, N'-((4-methyl-1H-imidazol-5-yl)methylidene)-3-phenyl-1H-indole-2-carbohydrazide, N'-((1-methyl-1H-imidazol-2-yl)methylidene)-3-phenyl-1H-indole-2-carbohydrazide, N'-((2-chloro-3-quinolinyl)methylidene)-3-phenyl-1H-indole-2-carbohydrazide, N'-((1-methyl-1H-pyrrol-2-yl)methylidene)-3-phenyl-1H-indole-2-carbohydrazide, N'-((4-chloro-1-methyl-1H-pyrazol-3-yl)methylidene)-3-phenyl-1H-indole-2-carbohydrazide, and N'-(3-chloro-5-(trifluoromethyl)-2-pyridinyl)methylidene)-3-phenyl-1H-indole-2-carbohydrazide.

28. A pharmaceutical composition comprising a compound of claim 1 or a therapeutically acceptable salt thereof, in combination with a therapeutically acceptable carrier.

29. A method of inhibiting angiogenesis in a mammal in recognized need of such treatment comprising administering to the mammal a therapeutically acceptable amount of a compound of claim 1, or a therapeutically acceptable salt thereof.

30. A compound selected from the group consisting of

N'-((4-methoxyphenyl)methylidene)-3-phenyl-1H-indole-2-carbohydrazide,

N'-((4-bromophenyl)methylidene)-3-phenyl-1H-indole-2-carbohydrazide, 3-phenyl-N'-((4-(trifluoromethoxy)phenyl)methylidene)-1H-indole-2-carbohydrazide, N'-((4-(difluoromethoxy)phenyl)methylidene)-3-phenyl-1H-indole-2-carbohydrazide, N'-((3-bromophenyl)methylidene)-3-phenyl-1H-indole-2-carbohydrazide, N'-((4-(dihydroxyamino)phenyl)methylidene)-3-phenyl-1H-indole-2-carbohydrazide, 3-phenyl-N'-(phenylmethylidene)-1H-indole-2-carbohydrazide, N'-((3-cyanophenyl)methylidene)-3-phenyl-1H-indole-2-carbohydrazide, N'-((4-methoxyphenyl)methylidene)-3-methyl-1H-indole-2-carbohydrazide, N'-((4-cyanophenyl)methylidene)-3-phenyl-1H-indole-2-carbohydrazide, N-(4-((2-((3-phenyl-1H-indol-2-yl)carbonyl)hydrazono)methyl)phenyl)-acetamide, N'-((4-(diethylamino)phenyl)methylidene)-3-phenyl-1H-indole-2-carbohydrazide, N'-((4-isopropylphenyl)methylidene)-3-phenyl-1H-indole-2-carbohydrazide, N'-((3-nitrophenyl)methylidene)-3-phenyl-1H-indole-2-carbohydrazide, 3-phenyl-N'-((4-(1-pyrrolidinyl)phenyl)methylidene)-1H-indole-2-carbohydrazide, N'-((4-(methylsulfonyl)phenyl)methylidene)-3-phenyl-1H-indole-2-carbohydrazide, N'-(butylidene)-3-phenyl-1H-indole-2-carbohydrazide, N'-(pentylidene)-3-phenyl-1H-indole-2-carbohydrazide, N'-((4-chlorophenyl)methylidene)-3-phenyl-1H-indole-2-carbohydrazide, N'-((4-bromophenyl)methylidene)-3-isopropyl-1H-indole-2-carbohydrazide, N'-((4-chlorophenyl)methylidene)-3-isopropyl-1H-indole-2-carbohydrazide, N'-((4-fluorophenyl)methylidene)-3-isopropyl-1H-indole-2-carbohydrazide, N'-((4-cyanophenyl)methylidene)-3-isopropyl-1H-indole-2-carbohydrazide, N'-((4-cyanophenyl)methylidene)-5-fluoro-3-phenyl-1H-indole-2-carbohydrazide, N'-((4-cyanophenyl)methylidene)-5-methoxy-3-phenyl-1H-indole-2-carbohydrazide, 5-bromo-N'-((4-cyanophenyl)methylidene)-3-phenyl-1H-indole-2-carbohydrazide, 3-isopropyl-N'-(phenylmethylidene)-1H-indole-2-carbohydrazide, 5-methoxy-3-phenyl-N'-(phenylmethylidene)-1H-indole-2-carbohydrazide, 5-bromo-3-phenyl-N'-(phenylmethylidene)-1H-indole-2-carbohydrazide, 3-isopropyl-N'-((4-nitrophenyl)methylidene)-1H-indole-2-carbohydrazide, N'-(1-naphthylmethylidene)-3-phenyl-1H-indole-2-carbohydrazide, 3-phenyl-N'-((4-(trifluoromethyl)phenyl)methylidene)-1H-indole-2-carbohydrazide, 3-phenyl-N'-(4-quinolinylmethylidene)-1H-indole-2-carbohydrazide, methyl 4-((((3-phenyl-1H-indol-2-yl)carbonyl)hydrazono)methyl)benzoate, N'-((4-bromophenyl)methylidene)-3-(4-fluorophenyl)-1H-indole-2-carbohydrazide, N'-((4-chlorophenyl)methylidene)-3-(4-fluorophenyl)-1H-indole-2-carbohydrazide, 3-(4-fluorophenyl)-N'-((4-nitrophenyl)methylidene)-1H-indole-2-carbohydrazide, N'-((4-cyanophenyl)methylidene)-3-(4-fluorophenyl)-1H-indole-2-carbohydrazide, 3-(4-chlorophenyl)-N'-((4-cyanophenyl)methylidene)-1H-indole-2-carbohydrazide, N'-((4-bromophenyl)methylidene)-3-(4-chlorophenyl)-1H-indole-2-carbohydrazide, 3-(4-chlorophenyl)-N'-((4-chlorophenyl)methylidene)-1H-indole-2-carbohydrazide,
3-(4-chlorophenyl)-N'-((4-nitrophenyl)methylidene)-1H-indole-2-carbohydrazide,
N'-((4-bromo-3,5-dimethoxyphenyl)methylidene)-3-phenyl-1H-indole-2-carbohydrazide,
N'-((3,4-dichlorophenyl)methylidene)-3-phenyl-1H-indole-2-carbohydrazide,
N'-((4-bromo-2-fluorophenyl)methylidene)-3-phenyl-1H-indole-2-carbohydrazide,
N'-((2,4-dichlorophenyl)methylidene)-3-phenyl-1H-indole-2-carbohydrazide,
N'-((4-chloro-3-nitrophenyl)methylidene)-3-phenyl-1H-indole-2-carbohydrazide,
N'-((4-fluorophenyl)methylidene)-3-methyl-1H-indole-2-carbohydrazide,
N'-((4-cyanophenyl)methylidene)-3-(3,4-dimethylphenyl)-1H-indole-2-carbohydrazide,
N'-((4-chlorophenyl)methylidene)-3-(3,4-dimethylphenyl)-1H-indole-2-carbohydrazide,
3-(3,4-dimethylphenyl)-N'-((4-nitrophenyl)methylidene)-1H-indole-2-carbohydrazide,
3-(3,4-dimethylphenyl)-N'-((4-fluorophenyl)methylidene)-1H-indole-2-carbohydrazide,
3-phenyl-N'-(4-pyridinylmethylidene)-1H-indole-2-carbohydrazide,
3-phenyl-N'-(3-pyridinylmethylidene)-1H-indole-2-carbohydrazide,
3-phenyl-N'-(2-pyridinylmethylidene)-1H-indole-2-carbohydrazide,
N'-((6-methyl-2-pyridinyl)methylidene)-3-phenyl-1H-indole-2-carbohydrazide,
3-methyl-N'-(phenylmethylidene)-1H-indole-2-carbohydrazide,
N'-((4-bromophenyl)methylidene)-3-methyl-1H-indole-2-carbohydrazide,
N'-((4-cyanophenyl)methylidene)-3-methyl-1H-indole-2-carbohydrazide,
N'-(3-furylmethylidene)-3-phenyl-1H-indole-2-carbohydrazide,
N'-((5-methyl-2-furyl)methylidene)-3-phenyl-1H-indole-2-carbohydrazide,
N'-(1-benzofuran-2-ylmethylidene)-3-phenyl-1H-indole-2-carbohydrazide,
N'-((5-nitro-2-furyl)methylidene)-3-phenyl-1H-indole-2-carbohydrazide,
N'-(2-furylmethylidene)-3-phenyl-1H-indole-2-carbohydrazide,
3-isopropyl-N'-((5-nitro-2-furyl)methylidene)-1H-indole-2-carbohydrazide,
3-isopropyl-N'-((5-methyl-2-furyl)methylidene)-1H-indole-2-carbohydrazide,
3-isopropyl-N'-(3-pyridinylmethylidene)-1H-indole-2-carbohydrazide,
N'-(2-furylmethylidene)-3-isopropyl-1H-indole-2-carbohydrazide,
3-methyl-N'-((5-nitro-2-furyl)methylidene)-1H-indole-2-carbohydrazide,
3-methyl-N'-((5-methyl-2-furyl)methylidene)-1H-indole-2-carbohydrazide,
3-methyl-N'-(3-pyridinylmethylidene)-1H-indole-2-carbohydrazide,
N'-(2-furylmethylidene)-3-methyl-1H-indole-2-carbohydrazide,
3-phenyl-N'-(1,3-thiazol-2-ylmethylidene)-1H-indole-2-carbohydrazide,
N'-((4,5-dimethyl-2-furyl)methylidene)-3-phenyl-1H-indole-2-carbohydrazide,
N'-((5-(4-methylphenyl)-2-furyl)methylidene)-3-phenyl-1H-indole-2-carbohydrazide,
N'-((5-ethyl-2-furyl)methylidene)-3-phenyl-1H-indole-2-carbohydrazide,
(5-((2-((3-phenyl-1H-indol-2-yl)carbonyl)hydrazono)methyl)-2-furyl)methyl acetate,
N'-((5-(4-nitrophenyl)-2-furyl)methylidene)-3-phenyl-1H-indole-2-carbohydrazide,
N'-((4-methyl-1H-imidazol-5-yl)methylidene)-3-phenyl-1H-indole-2-carbohydrazide,
N'-(1H-imidazol-2-ylmethylidene)-3-phenyl-1H-indole-2-carbohydrazide,
N'-((1-methyl-1H-imidazol-2-yl)methylidene)-3-phenyl-1H-indole-2-carbohydrazide,
N'-(1H-imidazol-5-ylmethylidene)-3-phenyl-1H-indole-2-carbohydrazide,
N'-((2-chloro-3-quinolinyl)methylidene)-3-phenyl-1H-indole-2-carbohydrazide,
3-phenyl-N'-(1H-pyrrol-2-ylmethylidene)-1H-indole-2-carbohydrazide,
N'-((1-methyl-1H-pyrrol-2-yl)methylidene)-3-phenyl-1H-indole-2-carbohydrazide,
N'-((4-chloro-1-methyl-1H-pyrazol-3-yl)methylidene)-3-phenyl-1H-indole-2-carbohydrazide,
N'-((4-(difluoromethoxy)phenyl)methylidene)-3-methyl-1H-indole-2-carbohydrazide,
4-((((3-isopropyl-1H-indol-2-yl)carbonyl)hydrazono)methyl)benzamide,
N'-((4-fluorophenyl)methylidene)-3-vinyl-1H-indole-2-carbohydrazide,
4-((((3-phenyl-1H-indol-2-yl)carbonyl)hydrazono)methyl)benzenesulfonamide,
N'-((4-hydroxyphenyl)methylidene)-3-phenyl-1H-indole-2-carbohydrazide,
4-((((3-phenyl-1H-indol-2-yl)carbonyl)hydrazono)methyl)phenyl sulfamate,
N'-(3-chloro-5-(trifluoromethyl)-2-pyridinyl)methylidene)-3-phenyl-1H-indole-2-carbohydrazide,
N'-((4-chloro-1,3-thiazol-2-yl)methylidene)-3-isopropyl-1H-indole-2-carbohydrazide,
3-isopropyl-N'-(3-thienylmethylidene)-1H-indole-2-carbohydrazide,
3-isopropyl-N'-(2-thienylmethylidene)-1H-indole-2-carbohydrazide,
3-isopropyl-N'-((3-methyl-2-thienyl)methylidene)-1H-indole-2-carbohydrazide,
N'-((5-chloro-2-thienyl)methylidene)-3-isopropyl-1H-indole-2-carbohydrazide, and
N'-(1-benzofuran-2-ylmethylidene)-3-isopropyl-1H-indole-2-carbohydrazide.

* * * * *